(12) United States Patent
Flerlage et al.

(10) Patent No.: US 11,983,947 B2
(45) Date of Patent: *May 14, 2024

(54) GENERATING DOCUMENT CONTENT BY DATA ANALYSIS

(71) Applicant: Clover Health, Jersey City, NJ (US)

(72) Inventors: David Ford Flerlage, San Francisco, CA (US); Joey P. Leingang, New York, NY (US)

(73) Assignee: Clover Health, Jersey City, NJ (US)

( * ) Notice: Subject to any disclaimer, the term of this patent is extended or adjusted under 35 U.S.C. 154(b) by 33 days.

This patent is subject to a terminal disclaimer.

(21) Appl. No.: 17/838,442

(22) Filed: Jun. 13, 2022

(65) Prior Publication Data

US 2022/0309817 A1    Sep. 29, 2022

Related U.S. Application Data

(63) Continuation of application No. 16/210,519, filed on Dec. 5, 2018, now Pat. No. 11,361,568.

(51) Int. Cl.
*G06V 30/414* (2022.01)
*G06V 30/412* (2022.01)
(Continued)

(52) U.S. Cl.
CPC .......... *G06V 30/414* (2022.01); *G06V 30/412* (2022.01); *G06V 30/416* (2022.01); *G16H 15/00* (2018.01)

(58) Field of Classification Search
CPC .. G06V 30/414; G06V 30/412; G06V 30/416; G16H 15/00; G16H 50/70
(Continued)

(56) References Cited

U.S. PATENT DOCUMENTS

| 8,731,968 | B1 * | 5/2014 | Iliff ..................... G16H 10/60 705/3 |
| 2002/0035486 | A1 | 3/2002 | Huyn et al. |

(Continued)

OTHER PUBLICATIONS

Non Final Office Action dated Sep. 2, 2020 for U.S. Appl. No. 16/210,519, "Generating Document Content by Data Analysis", Flerlage, 23 pages.

(Continued)

*Primary Examiner* — Shahid K Khan
*Assistant Examiner* — Ahamed I Nazar
(74) *Attorney, Agent, or Firm* — Lee & Hayes P.C.

(57) ABSTRACT

Systems and methods for generating document content using data analysis. For example, a system may store data representing one or more documents, where a document is associated with a type of user and fields. The system may send the data representing the document to an electronic device. Additionally, the system may receive, from the electronic device, data representing information input into the document. Using the information, the system may select various fields for the document and send, to the electronic device, data representing the fields. Furthermore, the system may analyze the information to determine a score associated with the document. If the score does not satisfy a threshold score, the system may continue to select fields using the information and send, to the electronic device, data representing the fields. However, if the score satisfies the threshold score, the system may determine that the document is complete.

20 Claims, 12 Drawing Sheets

(51) Int. Cl.
*G06V 30/416* (2022.01)
*G16H 15/00* (2018.01)

(58) Field of Classification Search
USPC .......................................................... 715/209
See application file for complete search history.

(56) References Cited

U.S. PATENT DOCUMENTS

| | | |
|---|---|---|
| 2002/0040183 A1 | 4/2002 | Iliff |
| 2002/0068857 A1 | 6/2002 | Iliff |
| 2002/0160347 A1 | 10/2002 | Wallace et al. |
| 2005/0192487 A1 | 9/2005 | Cosentino et al. |
| 2008/0052318 A1 | 2/2008 | Iliff |
| 2009/0007924 A1 | 1/2009 | Iliff |
| 2009/0210251 A1* | 8/2009 | Callas .................... G06Q 10/10 705/2 |
| 2011/0093281 A1 | 4/2011 | Plummer et al. |
| 2012/0221251 A1 | 8/2012 | Rosenberg et al. |
| 2012/0290310 A1* | 11/2012 | Watson .................. G16H 10/60 706/50 |
| 2013/0297344 A1 | 11/2013 | Cosentino et al. |
| 2014/0298165 A1 | 10/2014 | Hussam |
| 2016/0086135 A1 | 3/2016 | Tomonaga et al. |
| 2018/0046764 A1 | 2/2018 | Katwala et al. |
| 2020/0184209 A1 | 6/2020 | Flerlage et al. |

OTHER PUBLICATIONS

Office Action for U.S. Appl. No. 16/210,519, dated Oct. 15, 2021, Flerlage, "Generating Document Content by Data Analysis", 5 Pages.

Office Action for U.S. Appl. No. 16/210,519, dated Mar. 19, 2021, Flerlage, "Generating Document Content by Data Analysis", 34 pages.

The PCT Search Report and Written Opinion dated Mar. 30, 2020 for PCT Application No. PCT/US19/64493, 8 pages.

* cited by examiner

GENERATING DOCUMENT CONTENT BY DATA ANALYSIS

CROSS-REFERENCE TO RELATED APPLICATION

This patent application is a continuation of and claims priority to U.S. Utility patent application Ser. No. 16/210,519, filed Dec. 5, 2018, which is fully incorporated herein by reference.

BACKGROUND

In order to receive information about a user, such as a patient being examined, the information may be input into a document. For example, the document may ask a series of questions in order to obtain the information, such as the user's name, age, weight, symptoms, test results, and so forth. Once the information is input into the document, the information may be analyzed by another user, such as a doctor, in order to diagnosis the patient. However, different patients may have different diagnoses and as such, a system may be required to store documents that include questions related to multiple diagnoses. This can cause problems, as computer code must be generated for each of the documents, which can require computing resources. Additionally, storing the data for each of the documents can require a lot of memory.

Furthermore, information may be input into a document that is not relevant to an actual diagnosis of a user. For example, if the user has heart disease, the document will include questions related to heart disease as well as other diagnoses, such as cancer or diabetes. This additional information may make it more difficult to diagnose the user, since it is not actually relevant to the actual diagnosis.

BRIEF DESCRIPTION OF THE DRAWINGS

The detailed description is set forth below with reference to the accompanying figures. In the figures, the left-most digit(s) of a reference number identifies the figure in which the reference number first appears. The use of the same reference numbers in different figures indicates similar or identical items. The systems depicted in the accompanying figures are not to scale and components within the figures may be depicted not to scale with each other.

DETAILED DESCRIPTION

Figure 1:
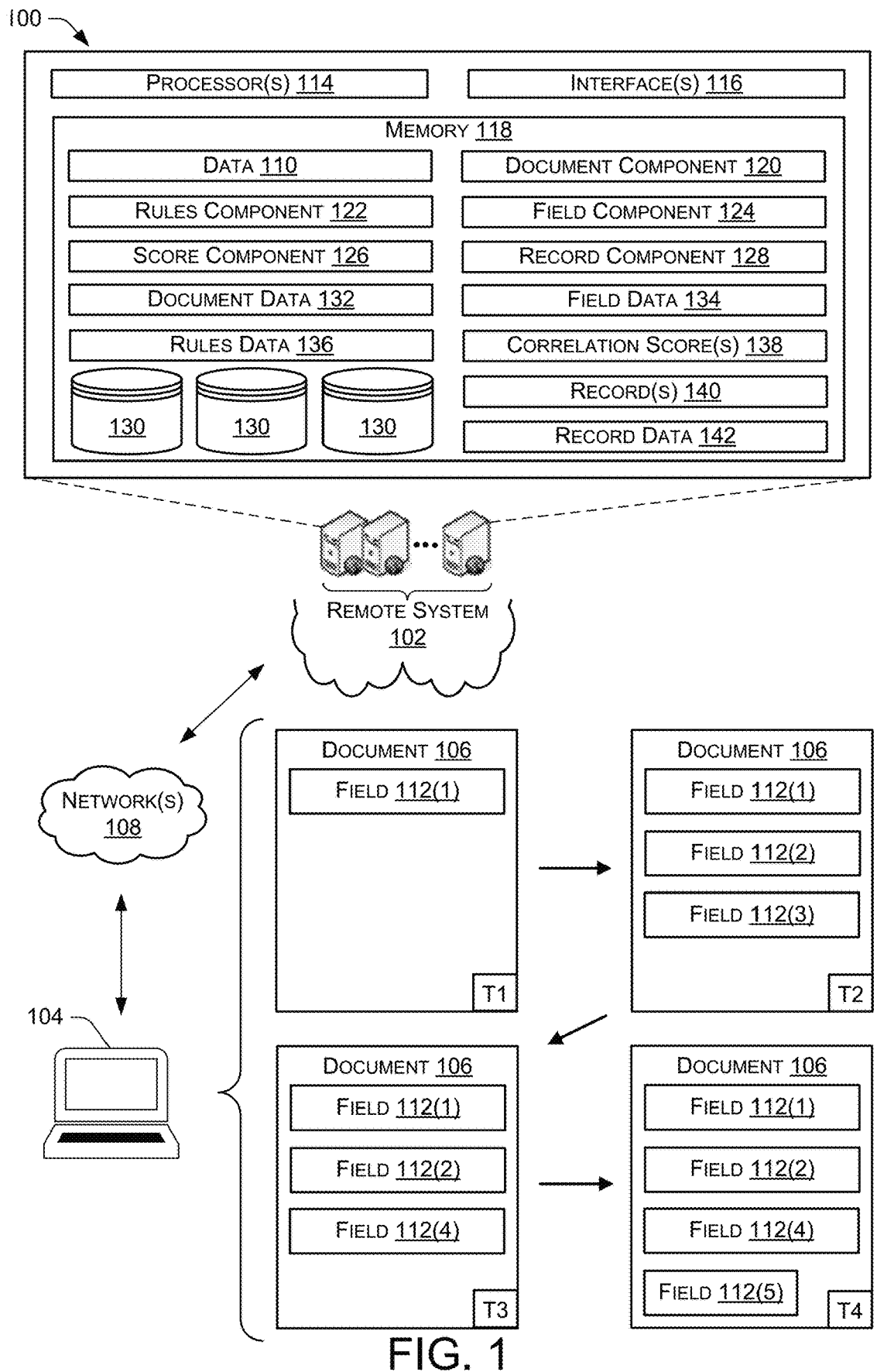
FIG. 1 illustrates a schematic diagram of an example environment for generating document content by data analysis, according to various examples of the present disclosure.

The present application is directed to systems and methods for generating document content using data analysis. For example, an entity, such as a user, group, business, corporation, medical facility, and/or so forth, can use documents to obtain information. In some examples, a document can include a number of fields (e.g., properties, elements, etc.), where a field can be updated with information that is relevant to the field. For example, an employee at a medical facility, such as a doctor or nurse, can use a document to determine information about a patient. The document can include a number of fields, where the employee inputs respective information into one or more of the fields. For example, the fields can include a first field associated with a name of the patient, a second field associated with an age of the patient, a third field associated with a weight of the patient, a fourth field associated with symptoms the patient is having, a fifth field associated with results of tests performed on the patient, and/or so forth. The employee can then input the information that is relevant to the fields into the document. Using the information, the employee and/or another employee can diagnose the patient.

In some examples, a system can store data representing various documents, where an individual document is associated with a type of user and/or one or more fields. For example, the system can store data representing a first document that doctors use to obtain information related to patients, where the first document is associated with first fields. The system can further store data representing a second document that nurses use to obtain information related to patients, where the second document is associated with second fields. Although these are just a couple of examples of documents that are specific to types of users in the medical industry, in other examples, the system can store documents that are specific to types of users in other industries. For examples, in the legal industry, the system can store data representing documents that associated with partner attorneys, associate attorneys, paralegals, and/or so forth.

In some examples, the system can further store data representing rules for selecting fields for a document. The rules can indicate relationships between fields, such that a field is selected based at least in part on information that is input into one or more other fields. For a first example, a first field can represent a question with at least two responses, where a first response is related to a second field and a second response is related to a third field. As such, a rule can indicate that (1) when the first response is selected for the first field, the second field is selected for the document and (2) when the second response is selected for the first field, the third field is selected for the document. For a second example, a first field can represent a question that is requesting information that includes a numerical value. A first range of values for the numerical value can be include a relationship to a second field and a second range of values for the numerical value can be related to a third field. As such, a rule can indicate that (1) when a numerical value that is included in the first range of values is input into the first field, the second field is selected for the document and (2) when a numerical value that is included in the second range of values is input into the first field, the third field is selected for the document. While these are just a couple of examples of rules, the system can store data representing other types of rules, which are described below.

The system can provide the documents to users so that the users can use the documents to obtain information. For example, the system can receive, from an electronic device, data representing a request for a document. In some examples, the data can further represent a type of user that is requesting the document. Using the data, the system can select a document for the user. For example, if the data represents the type of user, the system can select the document that is associated with the type of user. The system can then send, to the electronic device, data representing the selected document. In some examples, the document includes one or more initial fields which the user can use to input initial information. For example, if the user is a nurse obtaining information about a patient, the one or more initial fields can be related to questions asking about the patient's name, age, weight, and/or initial diagnosis.

As the user inputs the information into the fields, the system can receive, from the electronic device, data representing the information. The system can then analyze the information using the rules in order to select additional fields for the document. For a first example, an initial field can represent a question that includes a number of responses, where a rule indicates that (1) when a first response is selected for the initial field, a first additional field is selected for the document and (2) when a second response is selected for the initial field, a second additional field is selected for the document. Based at least in part on the analysis, the system can determine that the information represents the first response. The system can use the rule associated with the initial field to select the first additional field. For a second example, an initial field can represent a question that is requesting information that includes a numerical value, wherein a rule can indicate that (1) when the numerical value is included in a first range of values, a first additional field is selected for the document and (2) when the numerical value is included in a second range of values, a second additional field is selected for the document. Based at least in part on the analysis, the system can determine that the information represents a numerical value that is included in the first range of values. The system can the use the rule associated with the initial field to select the first additional field.

The system can send, to the electronic device, data representing the one or more additional fields. In some examples, the data can further represent a command to populate the document with the one or more additional fields. The system can then continue to receive, from the electronic device, data representing information that is input into the document (e.g., input into the one or more additional fields). Using the data and/or the rules, the system can continue to select one or more additional fields, using the techniques above. Additionally, the system can continue to send, to the electronic device, data representing the one or more additional fields and/or a command to populate the document with the one or more additional fields.

In some examples, while receiving the data representing the information input into the document, the system can analyze the information to determine a correlation score associated with the information. The system can then determine if the correlation score satisfies (e.g., is equal to or exceeds) a threshold score. Based at least in part on determining that the correlation score satisfies the threshold score, the system can refrain from selecting and/or providing additional fields for the document and/or the system can determine that document is complete. In some examples, the system determines the correlation score each time the system receives additional information that is input into a field of the document. In some examples, the system determines the correlation score when the system receives additional information that is input into two or more fields of the document.

For example, if the document is associated with diagnosing a patient, the system can analyze first information to determine a first correlation score indicating how closely the first information relates to standard information (e.g., symptoms and/or expected test results) associated with a diagnosis. Based at least in part on the first correlation score satisfying a threshold score, the system can refrain from selecting and/or providing additional fields for the document and/or the system can determine that document is complete. Additionally, in some examples, the system can determine the diagnosis for the patient. However, based at least in part on determining that the first correlation score does not satisfy (e.g., is less than) the threshold score, the system can select at least one additional field for the document. The system can then send, to the electronic device, data representing the at least one additional field and/or a command to populate the document with the at least one additional field.

The system can then receive, from the electronic device, second information related to the at least one additional field. Based at least in part on receiving the second information, the system can determine a second correlation score indicating how closely the first information and/or the second information relate to the standard information associated with the diagnosis. Based at least in part on the second correlation score satisfying the threshold score, the system can refrain from selecting and/or providing additional fields for the document and/or the system can determine that document is complete. Additionally, in some examples, the system can determine the diagnosis for the patient. However, based at least in part on determining that the second correlation score does not satisfy the threshold score, the system can continue to select at least one additional field for the document, determine at least one additional correlation score for the information input into the document, and determine whether the at least one additional correlation score satisfies the threshold score.

In some examples, when diagnosing a patient, the system can use the information to determine correlation score(s) associated with one or more other diagnoses. The system can then determine whether the correlation score(s) satisfy the threshold score. Based at least in part on determining that a correlation score associated with a diagnosis exceeds the threshold score, the system can diagnose the patient. Additionally, in some examples, the system can select additional fields that are associated with the diagnosis. The system can then send, to the electronic device, data representing the additional fields. Based at least in part on the additional fields, the system can then receive information that is related to the determined diagnosis.

In some examples, such as when time is a factor for completing the document, the system can determine a period of time associated with the document. For example, the system can receive, from the electronic device, data representing the period of time. The system can then use the period for time when selecting the fields for the document. For a first example, the system can select between first fields for a first period of time and second fields for a second, different period of time. In such an example, if the first period of time is less than the second period of time, at least some of the first fields can be related to questions with selectable responses, such that a user completing the document can quickly select a respective response for the first fields. Additionally, the second fields can be related to questions in which the user manually inputs the responses, which can take longer for the user to complete. However, the responses for the second fields can include more information.

For a second example, the system can use the period of time to determine a number of fields for the document. The system can then select the fields for the document based on the number of fields. For instance, if the number of fields is below a threshold number of fields (e.g., two fields, five fields, ten fields, etc.), then the system may select fields that request information associated with an initial diagnosis. However, if the number of fields exceeds the threshold number of fields, then the system may select fields that request information associated with the initial diagnosis as well as other similar diagnosis.

In some examples, the system can utilize previous reports (e.g., records) in order to select fields for the document and/or update the selected fields for the document. For a first example, and if the document is associated with a patient, the system can analyze information included in at least one previous report associated with the patient to determine a diagnosis (e.g., using correlation scores, using information indicating the diagnosis, etc.) for the patient. The system can then use the rules to select fields that are related to the diagnosis. For a second example, and again if the document is associated with a patient, the system can analyze information included in at least one previous report to update at least one field of the document such that the at least one field is tailored towards the patient. For instance, if the field is related to a question such as "How much do you weigh?", and the information included in the at least one previous report indicates that the patient previously weighed 120 pounds, then system can update the question to "Do you still weigh 120 pounds?".

For a third example, the system can store data representing a first report for a first patient and data representing a second report for a second patient, where the second report indicates a diagnosis for the second patient. The system can then analyze the first report with respect to the second report to identify at least one similarity between the first report and the second report. For instance, the at least one similarity can include that the first report and the second report each represent information indicating one or more common symptoms. Based at least in part on the at least one similarity, the system can diagnose the first patient (e.g., the first patient has the same health problem as the second patient). The system can then use the diagnosis as an initial diagnosis the next time that a document is being utilized to obtain information associated with the first patient.

In some examples, the system can determine that the document is complete. For a first example, the system can determine that a correlation score for the document satisfies a threshold score. For a second example, the system can receive, from the electronic device, data indicating that the document is complete. Still, for a third example, the system can determine that the period of time has elapsed. In either example, the system can generate a report related to the document. In some examples, the report can include data that represents the fields of the document and/or the information that was input into the fields of the document. The system can then store the report in one or more databases. Additionally, in some examples, the system can send the data representing the report to the electronic device and/or an additional electronic device.

In some examples, the system generates the report to include all of the fields and information that are included within the document. In some examples, the system generates the report to include a portion of the fields and information that are included within the document. For a first example, if the system determines a diagnosis using the document, the system may generate the report to include the fields and information that are included within the document and relevant to the diagnosis. For a second example, if the document includes sensitive information (e.g., personal information, mental health information, whether the user has certain medical diseases, etc.), then the system may generate the report to include the fields and information included within the document that are not related to the sensitive information.

In some examples, a user may select the fields and information that are included within the report. For instance, the system may receive data representing which fields and/or information from the document to include within the report. The system may then generate the report to include the fields and/or information indicated by the data. In some examples, the system may generate the report to include all of the fields and information from the document, but may "hide" some of the fields and/or information when sending the report to a user. For example, if a user is not authorized to view sensitive information included within the report, the system may cause the sensitive information to no longer be included within the report when sending the report to the user.

In some examples, the system may generate the report such that the fields and information are displayed using a tabular format. In some examples, the system may generate the report using other types of formats. In some examples, when viewing the report, a user may select the fields and information for which the user wishes to view. The system may then cause the report to display the selected fields and information while "hiding" other fields and information that were not selected by the user. As such, the user may utilize the report to easily find information that is relevant to how the user is using the report. Still, in some examples, a user may use the report to generate new rules that can later be used by the system to select fields for documents.

As described herein, a document can include a form (e.g., open ended form, close ended form, mixed open ended and close ended form, etc.), a spreadsheet, a report, a chart, a schedule, a transcript, a notice, a note, a file, an agreement, a book, and/or any other type of document. A document can be associated with one or more fields for inputting information. For a first example, a field can represent a question with one or more responses (e.g., information) for selection. For a second example, a field can represent a question and an interface element for inputting a response (e.g., information). Additionally, information can include one or more words, one or more numerical values, one or more symbols, one or more selectable responses, and/or any other type of information that can be input into a document.

In some examples, a document may be utilized to obtain information associated with a patient. For example, one or more of fields of the document may be associated with receiving initial information related to the patient (e.g., age, sex, weight, etc.). Additionally, one or more fields of the document may be associated with receiving information related to symptom(s) being experienced by the patient. Furthermore, one or more fields of the document may be associated with receiving information related to test(s) performed on the patient. In such examples, the information input into the document can be used diagnose the patient. For example, the remote system may analyze the information (e.g., the initial information, the symptom(s), the test result(s), etc.) to diagnose the patient.

In some examples, by performing the processes and/or techniques described above to select fields for populating a document, the system is not required to store data representing multiple documents. Rather, the system can store data representing a document and then select fields for populating the document as information is received from an electronic device. This can cause the system to store less data, which can improve the system. Additionally, the system is capable of providing a document that is more relevant to a diagnosis, since the fields (e.g., questions) included in the document are selected and/or updated based at least in part on information that is being input into the document. As such, the information input into the document and/or the data received by the system can be more relevant to the actual diagnosis.

Although the above description includes the system analyzing information input into a document to select fields and/or determine whether the document is complete, in some examples, one or more electronic devices can analyze the information input into the document to select fields and/or determine whether the document is complete.

FIG. 1 illustrates a schematic diagram of an example environment 100 for generating document content by data analysis, according to various examples of the present disclosure. The environment 100 can include a remote system 102 and an electronic device 104 that is inputting information into a document 106 over the course of a period of time, for example. In some examples, the remote system 102 represents a system that generates and/or acquires data associated with one or more documents and stores that data. The remote system 102 can further represent a system that generates document content using the received data. In some examples, the electronic device 104 can receive inputs from users and, based at least in part on the inputs, generate input data. The input data can indicate information that is input into the document 106.

The electronic device 104 can communicate with the remote system 102 via one or more networks 108. The communication can include sending and/or receiving of data 110 associated with the document 106. In some examples, the data 110 can represent the information that is input into the document 106 (e.g., the input data generated by the electronic device 104). For example, the remote system 102 can receive the data 110 when the electronic device 104 receives input indicating information to input into the document 106. In some examples, the data 110 can represent fields 112(1)-(5) to be populate the document 106.

The remote system 102 can include one or more components, such as, for example, processor(s) 114, network interface(s) 116, and memory 118. The memory 118 can include one or more components, such as, for example, a document component 120, a rules component 122, a field component 124, a score component 126, a report component 128, and one or more databases 130. The one or more databases 130 can be configured to store data received by the remote system 102. For example, the one or more data databases 130 can be configured to receive and store the data 110 received from the electronic device 104. In some examples, the one or more databases 130, and/or one or more other components of the remote system 102, can be configured to format the data for storage in the one or more databases 130 such that the data is associated with an identifier of the document 106. For example, the data 110 associated with the document 106 can be received from the electronic device 104. The electronic device 104 can send the data 110 in the same or differing formats and/or can send the data 110 with differing identification formats. The one or more databases 130 and/or other components of the remote system 102 can be configured to associate the data 110 such that the data 110 is associated with the proper document 106 in the one or more databases 130.

The document component 120 can be configured to generate documents and then store document data 132 representing the documents. In some examples, the document component 120 generates the documents using data 110 received from one or more electronic devices, such as the electronic device 104. For example, the data 110 can indicate one or more fields to include in the documents. In some examples, one or more of the documents can be associated with a type of user. For example, the remote system 102 can store document data 132 representing a first document that doctors use to obtain information related to patients. The remote system 102 can further store document data 132 representing a second document that nurses use to obtain information related to patients. Although these are just a couple of examples of documents that are specific to types of users in the medical industry, in other examples, the remote system 102 can store document data 132 representing documents that are specific to types of users in other industries. For examples, in the legal industry, the remote system 102 can store document data 132 representing documents that associated with partner attorneys, associate attorneys, paralegals, and/or so forth.

In some examples, the document component 120 can associate document data 132 representing a document with field data 134 representing one or more fields that can be included within the document. For example, the remote system 102 can associate the document data 132 representing the first document that doctors use to obtain information related to patients with field data 134 representing one or more first fields. As discussed herein, the one or more first fields can be initially included within the first document and/or added to the first document while the doctors are inputting information into the first document. Additionally, the remote system 102 can associate document data 132 representing the second document that nurses use to obtain information related to patients with field data representing one or more second fields. As discussed herein, the one or more second fields can be initially included within the second document and/or added to the second document while the nurses are inputting information into the second document.

The rules component 122 can be configured to generate rules data 136 representing one or more rules for selecting fields for a document. In some examples, the rules component 122 generates the rules data 136 based at least in part on data 110 received from one or more electronic devices, such as the electronic device 104. For example, the data 110 can represent a rule, and the rules component 122 can store the data 110 as rules data 136 in the memory 118.

The rules can indicate relationships between fields, which the remote system 102 utilizes in order to select fields for a document. For a first example, a first field can represent a question with at least two responses, where a first response is related to a second field and a second response is related to a third field. As such, a rule can indicate that (1) when the first response is selected for the first field, the second field is selected for the document and (2) when the second response is selected for the first field, the third field is selected for the document. For a second example, a first field can represent a question that is requesting information that includes a numerical value. A first range of values for the numerical value can relate to a second field and a second range of values for the numerical value can related to a third field. As such, a rule can indicate that (1) when a numerical value that is included in the first range of values is input into the first field, the second field is selected for the document and (2) when a numerical value that is included in the second range of values is input into the first field, the third field is selected for the document.

In some examples, the rules can structure the fields similar to a "tree structure". For example, a first level (e.g., first step) of the tree structure can include one or more first fields. At least one of the one or more first fields can include one or more "branches" that connect to one or more second fields located on a second level (e.g., a second step) of the tree structure. Additionally, at least one of the second fields can include one or more "branches" that connect to one or more third fields located on a third level (e.g., a third step) of the tree structure. This can continue for one or more additional steps throughout the tree structure. In some examples, a "branch" that connects two fields together can represent an association (e.g., a rule) between the two fields. An example tree structure is described below with regard to FIG. 6.

In the example of FIG. 1, the remote system 102 can receive, from the electronic device 104, data 110 representing a request for the document 106. In some examples, the data 110 can indicate an identifier associated with the document 106. The identifier can include, but is not limited to, a name, a numerical identifier, an alphabetic identifier, a mixed numerical and alphabetic number, and/or any other type of identifier that can be used to identify the document 106. In some examples, the data 110 can further indicate a type of user that is requesting the document 106. The document component 120 can then utilize the data 110 to select the document 106. For a first example, if the data 110 indicates the identifier of the document 106, the document component 120 can match the identifier of the document 106 to document data 132 that also indicates the identifier of the document 106. Based on the match, the document component 120 can identify the document 106. For a second example, if the data 110 indicates the type of user, the document component 120 can match the type of user to document data 132 that also indicates the type of user. Based on the match, the document component 120 can identify the document 106. In either example, the remote system 102 can then send, to the electronic device 104, the document data 132 representing the document 106.

The electronic device 104 can receive the document data 104 and display the document 106 to the user. In the example of FIG. 1, the document 106 at time T1 (e.g., the top-left illustration of the document 106) includes a first field 112(1). In some examples, such as when the document 106 is for obtaining information associated with a patient, the first field 112(1) can represent a question associated with an initial diagnosis of the patient (e.g., "What is your initial diagnosis?"). In such an example, the electronic device 104 can receive an input indicating the initial diagnosis (e.g., "Heart Disease"). The electronic device 104 can then input first information representing the initial diagnosis into the document 106 (e.g., into the first field 112(1)). Additionally, the electronic device 104 can send, to the remote system 102, data 110 representing the first information.

The remote system 102 can receive, from the electronic device 104, data 110 representing the first information input into the first field 112(1) (e.g., the initial diagnosis). The field component 124 can then be configured to select one or more additional fields to add to the document 106. To select the one or more additional fields, the field component 124 can analyze the first information using the rules data 136. For example, and continuing with the example above where the document 106 is for obtaining information associated with the patient, a rule can indicate that at least a second field 112(2) and a third field 112(3) are related the first field 112(1) when the first information input into the first field 112(1) indicates the initial diagnosis (e.g., Heart Disease). As such, and based at least in part on the first information and the rule, the field component 124 can select the second field 112(2) and the third field 112(3) for the document 106. The remote system 102 can then send, to the electronic device 104, field data 134 representing the second field 112(2) and the third field 112(3). Additionally, the remote system 102 can send, to the electronic device 104, additional data that includes a command to populate the document 106 with the second field 112(2) and the third field 112(3).

The electronic device 104 can receive the field data 134 and/or the additional data from the remote system 102. In the example of FIG. 1, at time T2 (e.g., the top-right illustration of the document 106), the electronic device 104 can then populate the document 106 with the second field 112(2) and the third field 112(3). In some examples, each of the second field 112(2) and the third field 112(3) can represent questions related to the first information input into the first field 112(1). For example, when the first information represents the initial diagnosis, each of the second field 112(2) and the third field 112(3) can represent questions related to obtaining information that can be used to determine whether the initial diagnosis is accurate. For examples, if the initial diagnosis includes "Heart Disease", then the second field 112(2) can represent a question such as "Have you had any chest pains?" and the third field 112(3) can represent a question such as "Have you felt nausea?". In other words, the second field 112(2) and the third field 112(3) are related to symptoms of heart disease.

The electronic device 104 can then receive an input indicating second information related to the second field 112(2) (e.g., which, in the example of FIG. 1, may indicate "Yes"). Based at least in part on the input, the electronic device 104 can input the second information into the document 106 (e.g., into the second field 112(2)). Additionally, the electronic device 104 can send, to the remote system 102, data 110 representing the second information.

The remote system 102 can receive, from the electronic device 104, the data 110 representing the second information input into the second field 112(2) (e.g., Yes). The field component 124 can then be configured to select one or more additional fields to add to the document 106. To select the one or more additional fields, the field component 124 can analyze the first information and/or the second information using the rules data 136. For example, and continuing with the example above where the document 106 is for obtaining information associated with the patient, a rule can indicate that at least a fourth field 112(4) is associated with the second field 112(2) when the second information input into the second field 112(2) indicates "Yes". Additionally, the rule (and/or another rule) can indicate that the third field 112(3) is no longer relevant when the second information input into the second field 112(2) indicates "Yes". As such, the field component 124 can select the fourth field 112(4) for the document 106. The remote system 102 can then send, to the electronic device 104, field data 134 representing the fourth field 112(4). Additionally, the remote system 102 can send, to the electronic device 104, additional data that includes a command to replace the third field 112(3) with the fourth field 112(4).

The electronic device 104 can receive the field data 134 and/or the additional data from the remote system 102. In the example of FIG. 1, at time T3 (e.g., the bottom-left illustration of the document 106), the electronic device 104 can remove the third field 112(3) from the document 106 and then populate the document 106 with the fourth field 112(4). In some examples, the fourth field 112(4) can represent a question related to the first information input into the first field 112(1) and/or the second information input into the second field 112(2). For example, when the first information represents the initial diagnosis and the second information represents a symptom of the initial diagnosis, the fourth field 112(4) can represent a question related to obtaining information to further determine if the symptom is in fact related to the initial diagnosis. For examples, if the initial diagnosis includes "Heart Disease" and the symptom includes "Chest Pains", then the fourth field 112(4) can represent a question such as "Have often do you experience chest pains?".

The electronic device 104 can then receive an input indicating third information related to the fourth field 112(4) (e.g., "Once a day"). Based at least in part on the input, the electronic device 104 can input the third information into the document 106 (e.g., into the fourth field 112(4)). Additionally, the electronic device 104 can send, to the remote system 102, data 110 representing the third information.

The remote system 102 can receive, from the electronic device 104, the data 110 representing the third information input into the fourth field 112(4) (e.g., "Once a day"). The field component 124 can then be configured to select one or more additional fields to add to the document 106. To select the one or more additional fields, the field component 124 can analyze the first information, the second information, and/or the third information using the rules data 136. For example, and continuing with the example above where the document 106 is for obtaining information associated with the patient, a rule can indicate that at least a fifth field 112(5) is associated with the fourth field 112(4) when the third information input into the fourth field 112(4) indicates that the patient experiences chest pains at least four times a week. As such, the field component 124 can select the fifth field 112(5) for the document 106. The remote system 102 can then send, to the electronic device 104, field data 134 representing the fifth field 112(5). Additionally, the remote system 102 can send, to the electronic device 104, additional data that includes a command to populate the document 106 with the fifth field 112(5).

The electronic device 104 can receive the field data 134 and/or the additional data from the remote system 102. In the example of FIG. 1, at time T4 (e.g., the bottom-right illustration of the document 106), the electronic device 104 can populate (e.g., add) the fifth field 112(5) to the document 106. In some examples, the fifth field 112(5) can represent a question related to the first information input into the first field 112(1), the second information input into the second field 112(2), and/or the third information input into the fourth field 112(4). For example, when the first information represents the initial diagnosis, the second information represents a symptom of the initial diagnosis, and the third information represents how often the patient experiences the symptom, the fifth field 112(5) can represent a question related to whether the symptom is caused by something other than the initial diagnosis. For examples, if the initial diagnosis includes "Heart Disease", the symptom includes "Chest Pains", and the frequency of the symptom includes "Once a day", then the fifth field 112(5) can represent a question such as "How often do you eat spicy food?".

The electronic device 104 can then receive an input indicating fourth information related to the fifth field 112(5) (e.g., "Twice a week"). Based at least in part on the input, the electronic device 104 can input the fourth information into the document 106 (e.g., into the fifth field 112(5)). Additionally, the electronic device 104 can send, to the remote system 102, data 110 representing the fourth information.

The remote system 102 and the electronic device 104 can continue to perform similar processes until the document 106 is complete. In some examples, to determine that the document 106 is complete, the score component 126 can be configured to determine correlation score(s) 138 associated with the document 106. The score component 126 can then determine whether the correlation score(s) 138 satisfy (e.g., is equal to or greater than) a threshold score. Based at least in part on determining that the correlation score(s) 138 do not satisfy (e.g., are less than) the threshold score, the remote system 102 can continue to provide additional fields in order to obtain additional information. Based at least in part on determining that the correlation score(s) 138 satisfy the threshold score, the remote system 102 can determine that the document 106 is complete. The remote system 102 can then refrain from providing the electronic device 104 with additional fields and/or send, to the electronic device 104, data indicating that the document 106 is complete.

In some examples, such as when the document 106 is for obtaining information associated with the patient, a correlation score 138 can indicate a likelihood that the patient in fact has the initial diagnosis. In some examples, the score component 126 can determine a respective correlation score 138 each time the remote system 102 receives data 110 representing information input into the document 106. In some examples, the score component 126 can determine a respective correlation score 138 each time the remote system 102 receives data 110 representing information that is input into a threshold number of fields (e.g., one, two, five, etc.).

For example, such as at time T2, and continuing with the example above where the document 106 is for obtaining information associated with the patient, the score component 126 may have determined a first correlation score 138 (e.g., 50) using the data 110 representing the second information input into the document 106. The first correlation score 138 can indicate a likelihood (e.g., 50%) that the patient has the initial diagnosis of heart disease. The score component 126 may then have determined that the first correlation score 138 does not satisfy a threshold score (e.g., 90). Based at least in part on the determination, the remote system 102 may have determined to continue providing fields for the document 106.

Later, such as at time T3, the score component 126 may have determined a second correlation score 138 (e.g., 75)

using the data 110 representing the second information input into the document 106 and the data 110 representing the third information input into the document 106. The second correlation score 138 can indicate a likelihood (e.g., 75%) that the patient has the initial diagnosis of heart disease. The score component 126 may then have determined that the second correlation score 138 still does not satisfy the threshold score (e.g., 90). Based at least in part on the determination, the remote system 102 may have determined to continue providing fields for the document 106.

Later, such as at time T4, the score component 126 may have determined a third correlation score 138 (e.g., 95) using the data 110 representing the second information input into the document 106, the data 110 representing the third information input into the document 106, and the data 110 representing the fourth information input into the document 106. The third correlation score 138 can indicate a likelihood (e.g., 95%) that the patient has the initial diagnosis of heart disease. The score component 126 may then have determined that the third correlation score 138 satisfies the threshold score (e.g., 90). Based at least in part on the determination, the remote system 102 may have determined that the document 106 is complete and/or that the patient has heart disease. The remote system 102 may then have sent, to the electronic device 104, data indicating that the document 106 is complete and/or data indicating that the patient has heart disease.

Although the above example describes using a range for correlation score(s) 138 that is between 0-100, in other examples, the score component 126 may utilize any other range. For example, the score component 126 may determine correlation score(s) that are between 0-10, where the threshold score includes a numerical value between 0-10.

Additionally, or alternatively, in some examples, the remote system 102 may determine that the document 106 is complete based at least in part on the elapse of a give period of time. For example, the remote system 102 can determine the period of time for obtaining information using the document 106. In some examples, the remote system 102 can determine the period of time by receiving, from the electronic device 104, data 110 indicating the period of time. In some examples, the remote system 102 can determine the period of time based at least in part on the type of document 106. For example, if the document 106 is being utilized by a nurse to obtain information from a patient, the remote system 102 can determine that the nurse is usually provided a first period of time for obtaining the information. Additionally, if the document 106 is being utilized by a doctor to obtain the information from the patient, the remote system 102 can determine that the doctor is usually provided a second, different period of time for obtaining the information.

In some examples, the remote system 102 can utilize the period of time to select one or more of the fields 112(1)-(5) for the document 106. For a first example, if the period of time is less than a threshold period of time (e.g., one minute, ten minutes, thirty minutes, and/or any other time period), the field component 124 can select fields that more specific to the initial diagnosis such that information that is more relevant to the initial diagnosis is input into the document 106. Additionally, if the period of time is greater than the threshold period of time, then the field component 124 can select fields that are specific to the initial diagnosis, but also select fields that are specific to other, possible diagnoses. By selecting such fields, the remote system 102 can determine if the initial diagnosis is correct. Additionally, if the initial diagnosis is not correct, the remote system 102 can determine a new diagnosis based at least in part on the information input into the document 106.

For a second example, the field component 124 may utilize the period of time to determine a number of fields to select for the document 106. The field component 124 can then use the number of fields when selecting the fields for the document 106. For instance, if the number of fields is less than a threshold number of fields (e.g., two fields, five fields, and/or any other number of fields), the field component 124 can select fields that more specific to the initial diagnosis such that information that is more relevant to the initial diagnosis is input into the document 106. Additionally, if the number of fields is greater than the threshold number of fields, then the field component 124 can select fields that are specific to the initial diagnosis, but also select fields that are specific to other, possible diagnoses. By selecting such fields, the remote system 102 can determine if the initial diagnosis is correct. Additionally, if the initial diagnosis is not correct, the remote system 102 can determine a new diagnosis based at least in part on the information input into the document 106.

Additionally, or alternatively, in some examples, the remote system 102 can determine that the document 106 is complete by receiving, from the electronic device 104, data 110 indicating that the document 106 is complete.

In some examples, such as when the document is complete, the report component 128 can be configured to generate a report 140 associated with the document 106. The report 140 can indicate one or more of the fields 112(1)-(5) and/or at least a portion of the information input into the document 106. For example, the report 140 can indicate the fields (1)-(5) as well as the first information, the second information, the third information, and the fourth information input into the document 106. In some examples, the report 140 can further indicate the correlation score(s) 138 that were calculated as the document 106 was being completed. The remote system 102 can then store, in the one or more databases 130, report data 142 representing the report 140. Additionally, the remote system 102 can send, to the electronic device 104 (and/or another electronic device), the report data 142 representing the report 140.

In some examples, the remote system 102 can utilize the report data 142 to determine fields for a new document. For example, if the same patient returns for another checkup, the field component 124 can analyze the report data 142 to determine the initial diagnosis for the patient. The field component 124 can then utilize the initial diagnosis to select one or more fields for the new document. By utilizing the report data 142 representing the previous report 140 to generate new documents for the patient, the remote system 102 is able to generate documents that obtain information that is more specific to the patient. This information can then be utilized to better help diagnose the patient.

As used herein, a processor, such as processor(s) 114, can include multiple processors and/or a processor having multiple cores. Further, the processors can comprise one or more cores of different types. For example, the processors can include application processor units, graphic processing units, and so forth. In one implementation, the processor can comprise a microcontroller and/or a microprocessor. The processor(s) 114 can include a graphics processing unit (GPU), a microprocessor, a digital signal processor or other processing units or components known in the art. Alternatively, or in addition, the functionally described herein can be performed, at least in part, by one or more hardware logic components. For example, and without limitation, illustrative types of hardware logic components that can be used include field-programmable gate arrays (FPGAs), application-specific integrated circuits (ASICs), application-specific standard products (ASSPs), system-on-a-chip systems (SOCs), complex programmable logic devices (CPLDs), etc. Additionally, each of the processor(s) 114 can possess its own local memory, which also can store program components, program data, and/or one or more operating systems.

The memory 118 can include volatile and nonvolatile memory, removable and non-removable media implemented in any method or technology for storage of information, such as computer-readable instructions, data structures, program component, or other data. Such memory 118 includes, but is not limited to, RAM, ROM, EEPROM, flash memory or other memory technology, CD-ROM, digital versatile disks (DVD) or other optical storage, magnetic cassettes, magnetic tape, magnetic disk storage or other magnetic storage devices, RAID storage systems, or any other medium which can be used to store the desired information and which can be accessed by a computing device. The memory 118 can be implemented as computer-readable storage media ("CRSM"), which can be any available physical media accessible by the processor(s) 114 to execute instructions stored on the memory 118. In one basic implementation, CRSM can include random access memory ("RAM") and Flash memory. In other implementations, CRSM can include, but is not limited to, read-only memory ("ROM"), electrically erasable programmable read-only memory ("EEPROM"), or any other tangible medium which can be used to store the desired information and which can be accessed by the processor(s) 114.

Further, functional components can be stored in the respective memories, or the same functionality can alternatively be implemented in hardware, firmware, application specific integrated circuits, field programmable gate arrays, or as a system on a chip (SoC). In addition, while not illustrated, each respective memory, such as memory 118, discussed herein can include at least one operating system (OS) component that is configured to manage hardware resource devices such as the network interface(s), the I/O devices of the respective apparatuses, and so forth, and provide various services to applications or components executing on the processors. Such OS component can implement a variant of the FreeBSD operating system as promulgated by the FreeBSD Project; other UNIX or UNIX-like variants; a variation of the Linux operating system as promulgated by Linus Torvalds; the FireOS operating system from Amazon.com Inc. of Seattle, Washington, USA; the Windows operating system from Microsoft Corporation of Redmond, Washington, USA; LynxOS as promulgated by Lynx Software Technologies, Inc. of San Jose, California; Operating System Embedded (Enea OSE) as promulgated by ENEA AB of Sweden; and so forth.

The network interface(s) 116 can enable communications between the components and/or devices shown in environment 100 and/or with one or more other remote systems, as well as other networked devices. Such network interface(s) 116 can include one or more network interface controllers (NICs) or other types of transceiver devices to send and receive communications over the network 108. For instance, each of the network interface(s) 116 can include a personal area network (PAN) component to enable communications over one or more short-range wireless communication channels. For instance, the PAN component can enable communications compliant with at least one of the following standards IEEE 802.15.4 (ZigBee), IEEE 802.15.1 (Bluetooth), IEEE 802.11 (WiFi), or any other PAN communication protocol. Furthermore, each of the network interface(s) 112 can include a wide area network (WAN) component to enable communication over a wide area network.

Figure 2:
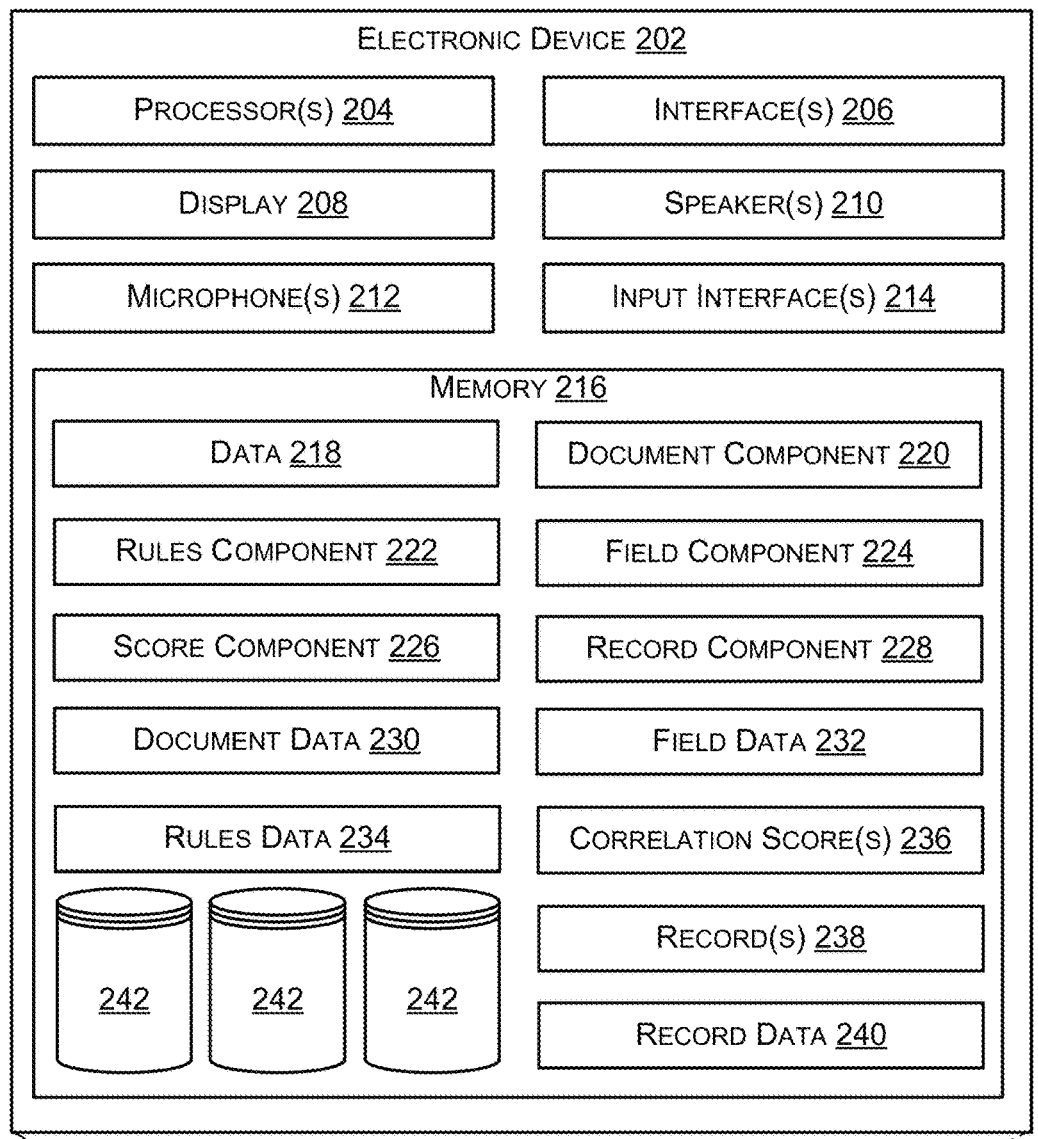
FIG. 2 illustrates a block diagram of an example electronic device that can generate document content by data analysis, according to various examples of the present disclosure.

Although the above description includes the remote system 102 generating the document 106, as well as performing the analysis to determine whether the document 106 is complete, in other examples, an electronic device can perform some and/or all of the processes and techniques described herein for the remote system 102. For example, FIG. 2 illustrates a block diagram of an example electronic device 202 that can generate document content by data analysis, according to various examples of the present disclosure. In some examples, the electronic device 202 can correspond to, and/or be similar to, the electronic device 104.

As shown, the electronic device 202 can include processor(s) 204 (which can correspond to, and/or be similar to, the processor(s) 114), network interface(s) 206 (which can correspond to, and/or be similar to, the network interface(s) 116), a display 208, speaker(s) 210, microphone(s) 212, input interface(s) 214 (a mouse, a trackball, a touchpad, a joystick, a pointing stick, a stylus, etc.), and a memory 216 (which can correspond to, and/or be similar to, the memory 1118). In some examples, the electronic device 202 may include additional components not shown in FIG. 2. Additionally, or alternatively, in some examples, the electronic device 202 may not include one or more of the components shown in FIG. 2.

As shown in the example of FIG. 2, the memory 216 can store data 218, a document component 220, a rule component 222, a field component 224, a score component 226, a report component 228, a document data 230, field data 232, rules data 234, correlation score(s) 236, report(s) 238, report data 240, and one or more databases 242. In some examples, the data 218, the document component 220, the rule component 222, the field component 224, the score component 226, the report component 228, the document data 230, the field data 232, the rules data 234, the correlation score(s) 236, the report(s) 238, the report data 240, and the one or more databases 242 can correspond respectively to, and/or be respectively similar to, the data 110, the document component 120, the rules component 122, the field component 124, the score component 126, the report component 128, the document data 132, the field data 134, the rules data 136, the correlation score(s) 138, the report(s) 140, the report data 142, and the one or more databases 130.

As discussed above, in some examples, the electronic device 202 can perform some and/or all of the processes of the remote system 102. For example, the electronic device 202 can utilize the document component 220 to select and/or provide (e.g., display) a document. The electronic device 202 can then utilize the field component 224 to select one or more fields for the document, using the processes described above. Furthermore, the electronic device 202 can utilize the score component 226 to calculate correlation score(s) 236 for the document, and then determine whether the correlation score(s) 236 satisfy a threshold score, using the processes described above. Moreover, the electronic device 202 can utilize the report component 228 to generate a report 238 for the document, using the processes described above.

While these are just a few examples of processes that can be performed by the electronic device 202, in some examples, the electronic device 202 can be capable of performing all of the processes described above with regard to the remote system 102. Additionally, in some examples, the remote system 102 can perform at least a first portion of the processes described above and the electronic device 202 can perform at least a second portion of the processes.

Figure 3:
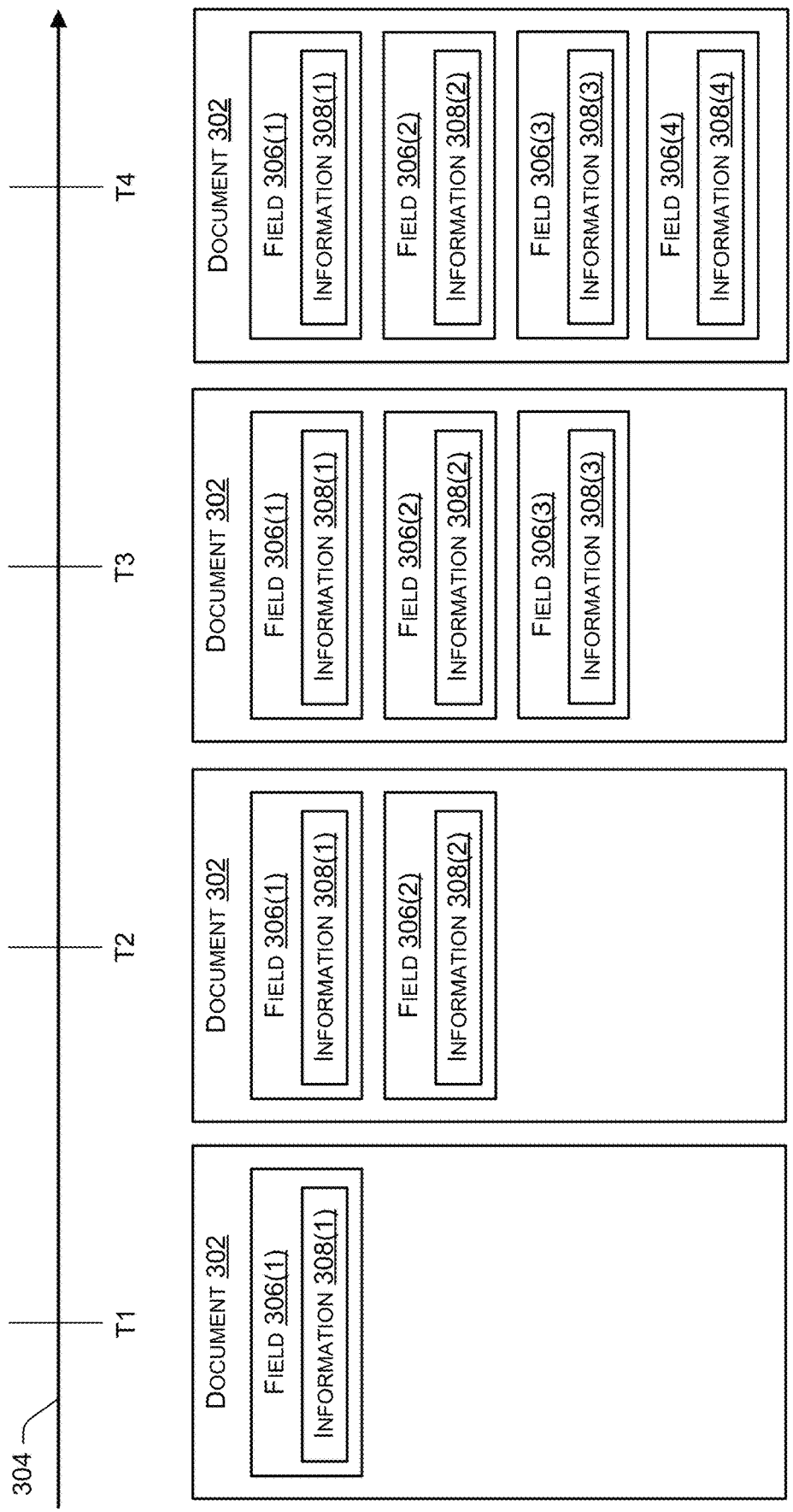
FIG. 3 illustrates a diagram of a first example of updating a document with fields as information is being input into the document, according to various examples of the present disclosure.

FIG. 3 illustrates a diagram of a first example of updating a document 302 with fields as information is being input into the document 302, according to various examples of the present disclosure. For example, over a period of time 304, the document 302 can be populated with fields 306(1)-(4) as information 308(1)-(4) is input into the document 302. For instance, at time 304 T1, the document 302 includes a first field 306(1). While displaying the first field 306(1), input representing first information 308(1) related to the first field 306(1) can be input into the document 302.

Based at least in part on the first information 308(1), the remote system 102 (and/or the electronic device 202) can select a second field 306(2) for the document 302. A such, at time 304 T2, the document 302 can be populated with the second field 306(2). While displaying the second field 306(2), input representing second information 308(2) related to the second field 306(2) can be input into the document 302.

Based at least in part on the first information 308(1) and/or the second information 308(2), the remote system 102 (and/or the electronic device 202) can select a third field 306(3) for the document 302. As such, at time 304 T3, the document 302 can be populated with the third field 306(3). While displaying the third field 306(3), input representing third information 308(3) related to the third field 306(3) can be input into the document 302.

Finally, based at least in part on the first information 308(1), the second information 308(2), and/or the third information 308(3), the remote system 102 (and/or the electronic device 202) can select a fourth field 306(4) for the document 302. As such, at time 304 T4, the document 302 can be populated with the fourth field 306(4). While displaying the fourth field 306(4), input representing fourth information 308(4) related to the fourth field 306(4) can be input into the document 302.

Figure 4:
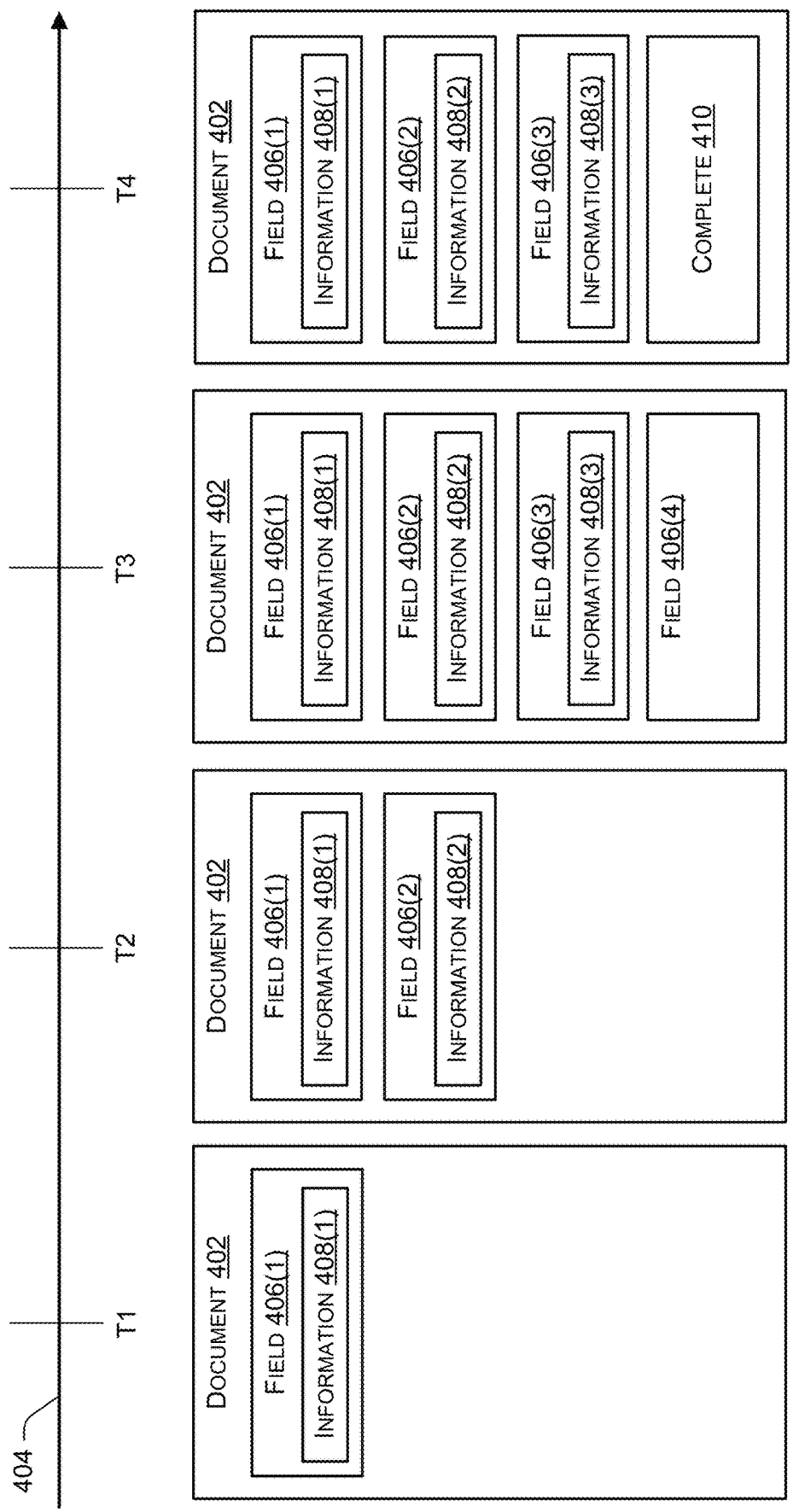
FIG. 4 illustrates a diagram of a second example of updating a document with fields as information is being input into the document, according to various examples of the present disclosure.

FIG. 4 illustrates a diagram of a second example of updating a document 402 with fields as information is being input into the document 402, according to various examples of the present disclosure. For example, over a period of time 404, the document 402 can be populated with fields 406(1)-(4) as information 408(1)-(3) is input into the document 402. For instance, at time 404 T1, the document 402 includes a first field 406(1). While displaying the first field 406(1), input representing first information 408(1) related to the first field 406(1) can be input into the document 402.

Based at least in part on the first information 408(1), the remote system 102 (and/or the electronic device 202) can determine a first correlation score associated with the document 402. In the example of FIG. 4, the remote system 102 (and/or the electronic device 202) can determine that the first correlation score does not satisfy a threshold score. As such, the remote system 102 (and/or the electronic device 202) can select a second field 406(2) for the document 402. As such, at time 404 T2, the document 402 can be populated with the second field 406(2). While displaying the second field 406(2), input representing second information 408(2) related to the second field 406(2) can be input into the document 402.

Based at least in part on the first information 408(1) and/or the second information 408(2), the remote system 102 (and/or the electronic device 202) can determine a second correlation score associated with the document 402. In the example of FIG. 4, the remote system 102 (and/or the electronic device 202) can determine that the second correlation score does not satisfy the threshold score. As such, the remote system 102 (and/or the electronic device 202) can select a third field 406(3) and a fourth field 406(4) for the document 402. As such, at time 404 T3, the document 402 can be populated with the third field 406(3) and the fourth field 406(4). While displaying the third field 406(3) and the fourth field 406(4), input representing third information 408(3) related to the third field 406(3) can be input into the document 402.

Finally, based at least in part on the first information 408(1), the second information 408(2), and/or the third information 408(3), the remote system 102 (and/or the electronic device 202) can determine a third correlation score associated with the document 402. In the example of FIG. 4, the remote system 102 (and/or the electronic device 202) can then determine that the third correlation score satisfies the threshold score. As such, the remote system 102 (and/or the electronic device 202) can determine that the document 402 is complete and/or information related to the fourth field 406(4) is no longer necessary. As such, at time 404 T4, the fourth field 406(4) can be removed from the document 402. Additionally, the document 402 can be populated with an indication that the document 402 is complete 410.

Figure 5:
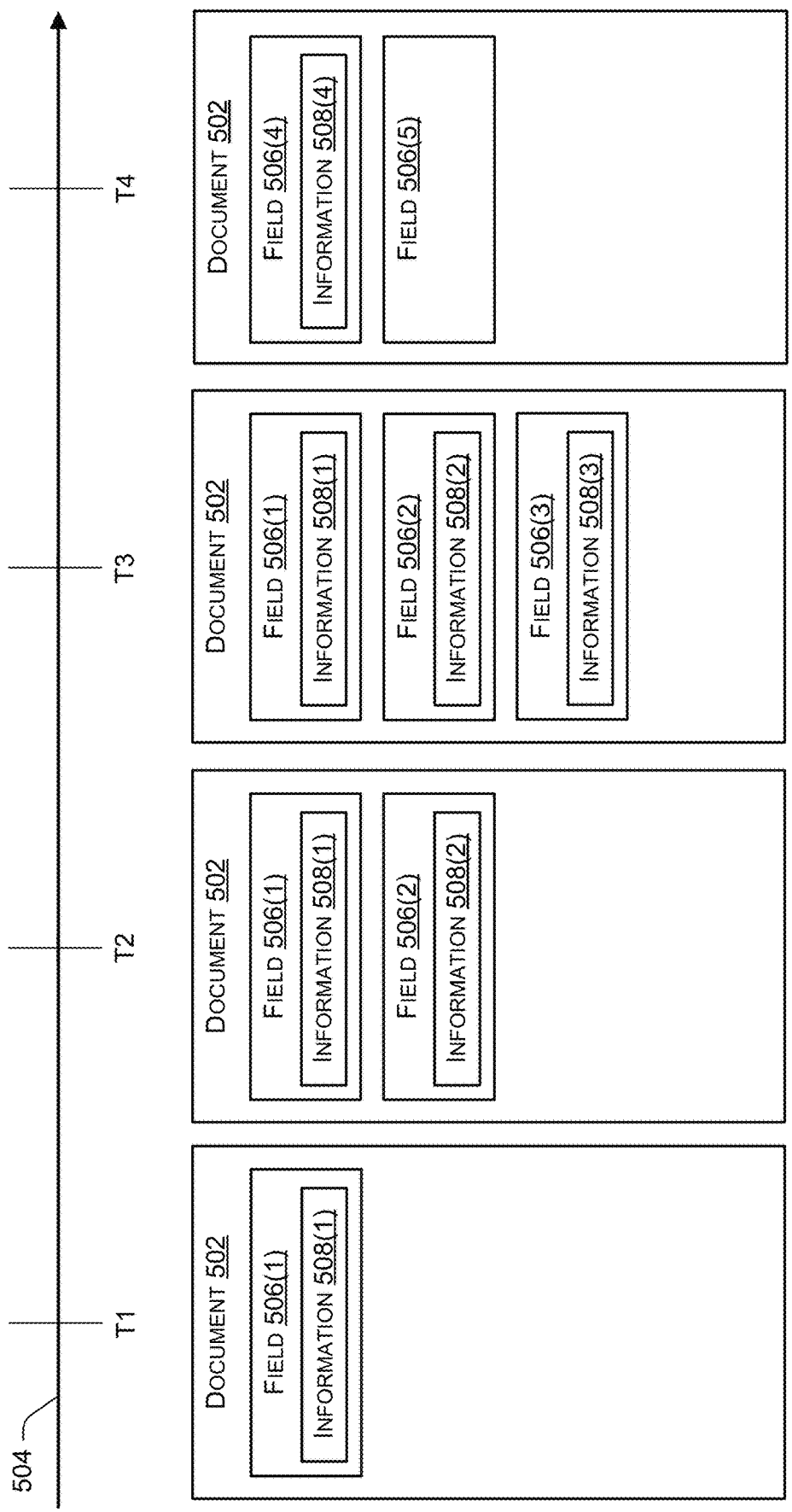
FIG. 5 illustrates a diagram of a third example of updating a document with fields as information is being input into the document, according to various examples of the present disclosure.

FIG. 5 illustrates a diagram of a third example of updating a document 502 with fields as information is being input into the document 502, according to various examples of the present disclosure. For example, over a period of time 504, the document 502 can be populated with fields 506(1)-(5) as information 508(1)-(4) is input into the document 502. For instance, at time 504 T1, the document 502 includes a first field 506(1). In the example of FIG. 5, the first field 506(1) can correspond to a question asking for an initial diagnosis. While displaying the first field 506(1), input representing first information 508(1) related to the first field 506(1) can be input into the document 502. For example, the first information 508(1) can be related to the initial diagnosis.

Based at least in part on the first information 508(1), the remote system 102 (and/or the electronic device 202) can determine a first correlation score associated with the document 502, where the first correlation score indicates a likelihood that a patient has the initial diagnosis. In the example of FIG. 5, the remote system 102 (and/or the electronic device 202) can determine that the first correlation score does not satisfy a threshold score. As such, the remote system 102 (and/or the electronic device 202) can select a second field 506(2) for the document 502. As such, at time 504 T2, the document 502 can be populated with the second field 506(2). While displaying the second field 506(2), input representing second information 508(2) related to the second field 506(2) can be input into the document 502.

Based at least in part on the first information 508(1) and/or the second information 508(2), the remote system 102 (and/or the electronic device 202) can determine a second correlation score associated with the document 502, where the second correlation score indicates a likelihood that the patient has the initial diagnosis. In the example of FIG. 5, the remote system 102 (and/or the electronic device 202) can determine that the second correlation score does not satisfy the threshold score. As such, the remote system 102 (and/or the electronic device 202) can select a third field 506(3) for the document 502. As such, at time 504 T3, the document 502 can be populated with the third field 506(3). While displaying the third field 506(3), input representing third information 508(3) related to the third field 506(3) can be input into the document 502.

Finally, based at least in part on the first information 508(1), the second information 508(2), and/or the third information 508(3), the remote system 102 (and/or the electronic device 202) can determine a third correlation score associated with the document 502, where the third correlation score indicates a likelihood that the patient has the initial diagnosis. In the example of FIG. 5, the remote system 102 (and/or the electronic device 202) can then determine that the third correlation score still does not satisfy the threshold score. Additionally, the remote system 102 (and/or the electronic device 202) can determine a fourth correlation score based at least in part on the first information 508(1), the second information 508(2), and/or the third information 508(3). The fourth correlation score can indicate a likelihood that the patient has a new diagnosis. The remote system 102 (and/or the electronic device 202) can then determine that the fourth correlation score satisfies a threshold score and/or that the fourth correlation score is greater than the third correlation score. Based at least in part on the determination(s), the remote system 102 (and/or the electronic device 202) can determine that the patient has the new diagnosis.

As such, the remote system 102 (and/or the electronic device 202) can select at least a fourth field 506(4) that includes fourth information 508(4) representing the new diagnosis. The remote system 102 (and/or the electronic device 202) can also select a fifth field 506(5) associated with the new diagnosis. As such, at time 504 T4, the document 502 can be populated with the fourth field 506(4), the fourth information 508(4), and the fifth field 506(5).

Figure 6:
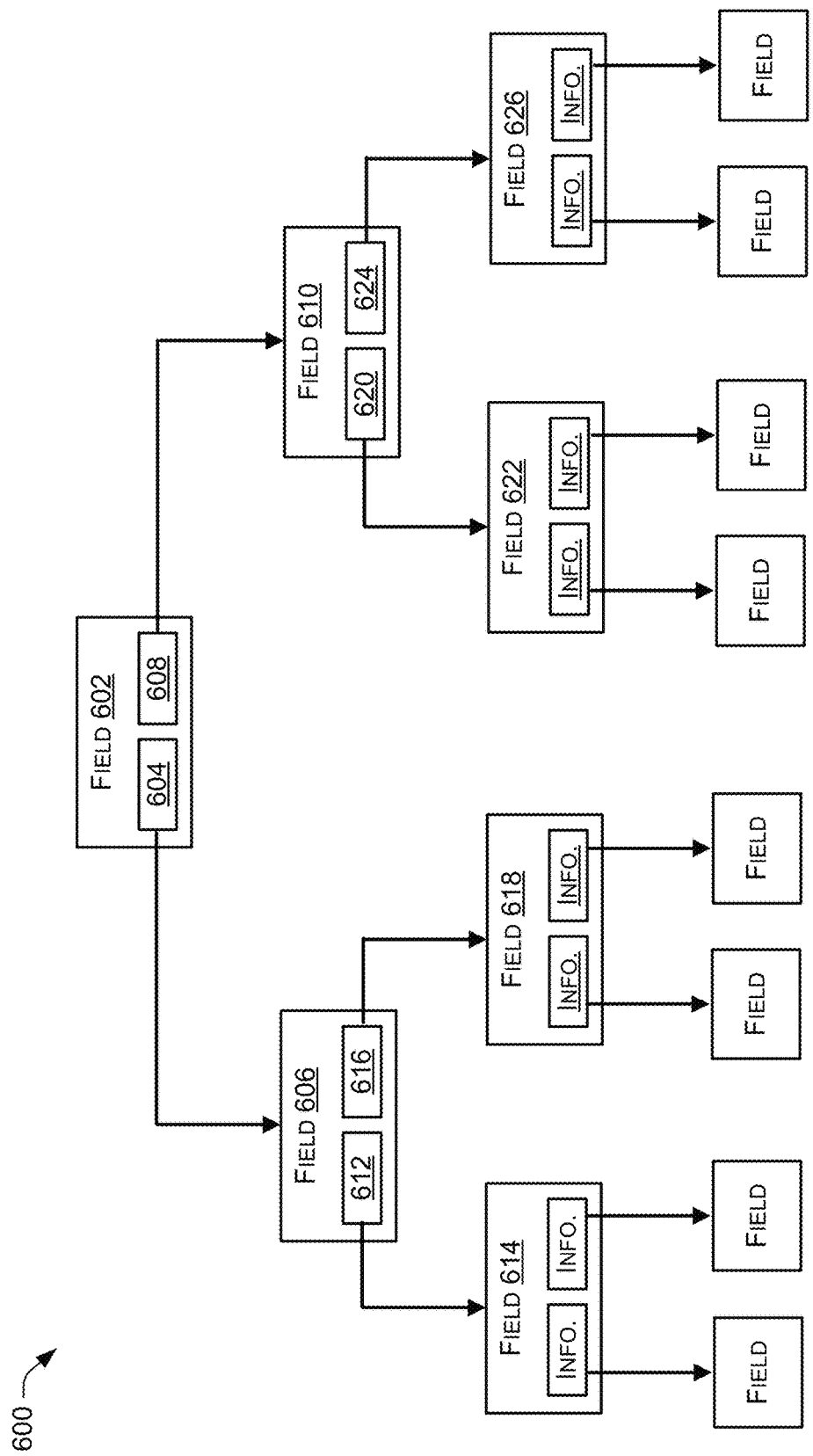
FIG. 6 illustrates a diagram of an example structure that may be utilized to select fields for a document, according to various examples of the present disclosure.

FIG. 6 illustrates a diagram of an example structure 600 that can be utilized to select fields for a document, according to various examples of the present disclosure. As shown, the structure 600 includes a first field 602 located at a first level (and/or first step) of the structure 600. A first rule associated with the structure 600 can indicate that if first information 604 is input into the first field 602, then a second field 606 is selected for the document. The first rule can further indicate that if second information 608 is input into the first field 602, then a third field 610 is selected for the document. The second field 606 and the third field 610 are located at a second level (and/or second step) of the structure 600.

Additionally, a second rule associated with the structure 600 can indicate that if third information 612 is input into the second field 606, then a fourth field 614 is selected for the document. The second rule can further indicate that if fourth information 616 is input into the third field 606, then a fifth field 618 is selected for the document. Furthermore, a third rule associated with the structure 600 can indicate that if fifth information 620 is input into the third field 610, then a sixth field 622 is selected for the document. The third rule can further indicate that if sixth information 624 is input into the third field 610, then a seventh field 626 is selected for the document. The fourth field 614, the fifth field 618, the sixth field 622, and the seventh field 626 are located in a third level (and/or third step) of the structure 600.

As shown in the example of FIG. 6, the structure 600 can continue such that new fields are selected when information is input a previous field in the structure 600. In some examples, although no illustrated in FIG. 6, the structure 600 can further be connected to another structure. For example, if the structure 600 is associated with a first diagnosis, and based at least in part on the information input into the document the remote system 102 (and/or the electronic device 202) identifies a second diagnosis, then the remote system (and/or the electronic device 202) can select a second structure associated with the second diagnosis.

Each of the processes described herein, including the processes 700, 800, 900, 1000, and 1100, are illustrated as a collection of blocks in a logical flow graph, which represent a sequence of operations that can be implemented in hardware, software, or a combination thereof. In the context of software, the blocks represent computer-executable instructions stored on one or more computer-readable storage media that, when executed by one or more processors, perform the recited operations. Generally, computer-executable instructions include routines, programs, objects, components, data structures, and the like that perform particular functions or implement particular abstract data types. The order in which the operations are described is not intended to be construed as a limitation, and any number of the described blocks can be combined in any order and/or in parallel to implement the processes. Additionally, any number of the described blocks can be optional and eliminated to implement the processes.

Figure 7A:
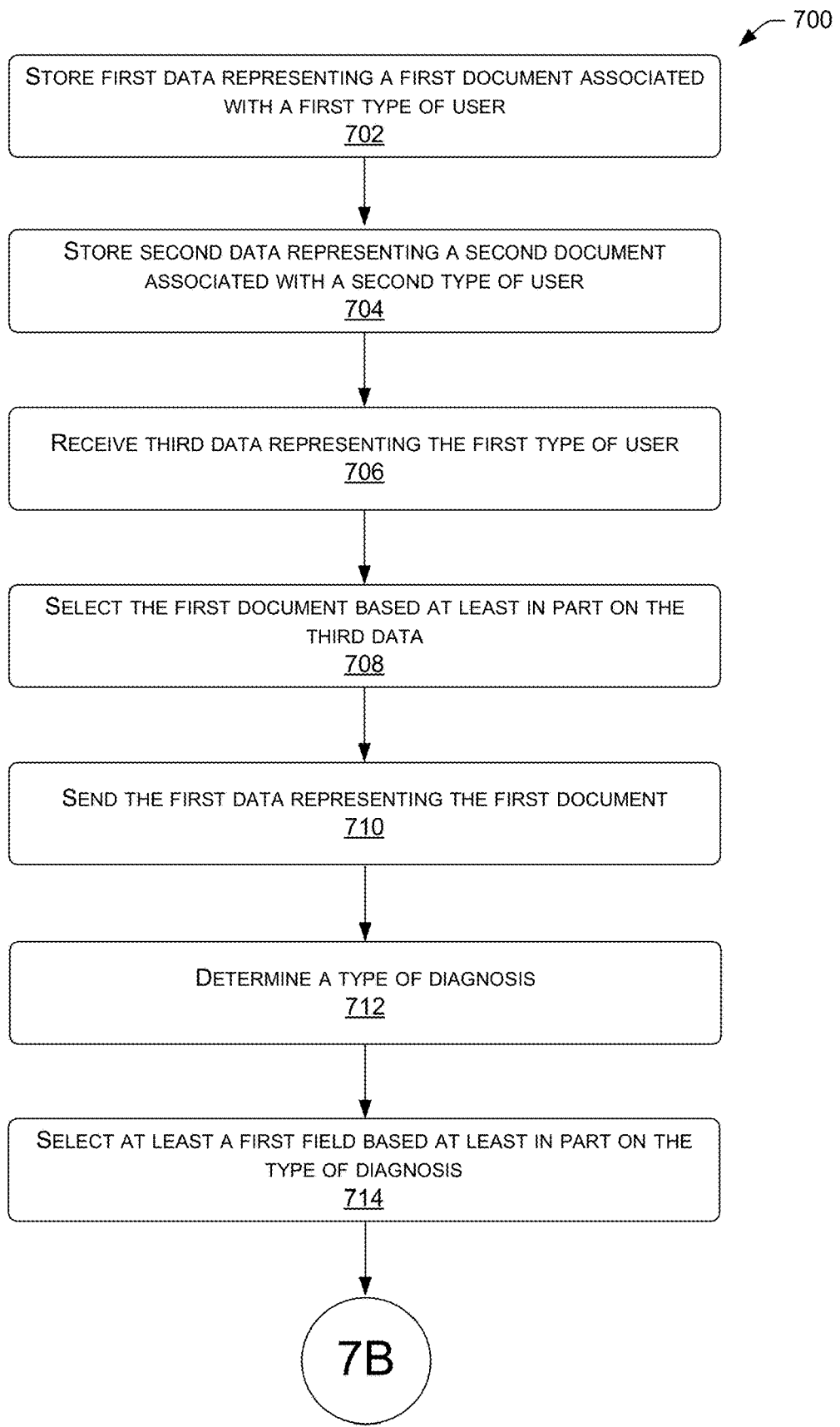
FIGS. 7A-7B illustrate a flow diagram of an example process for updating fields of a document as information is being input into the document, according to various examples of the present disclosure.
Figure 7B:
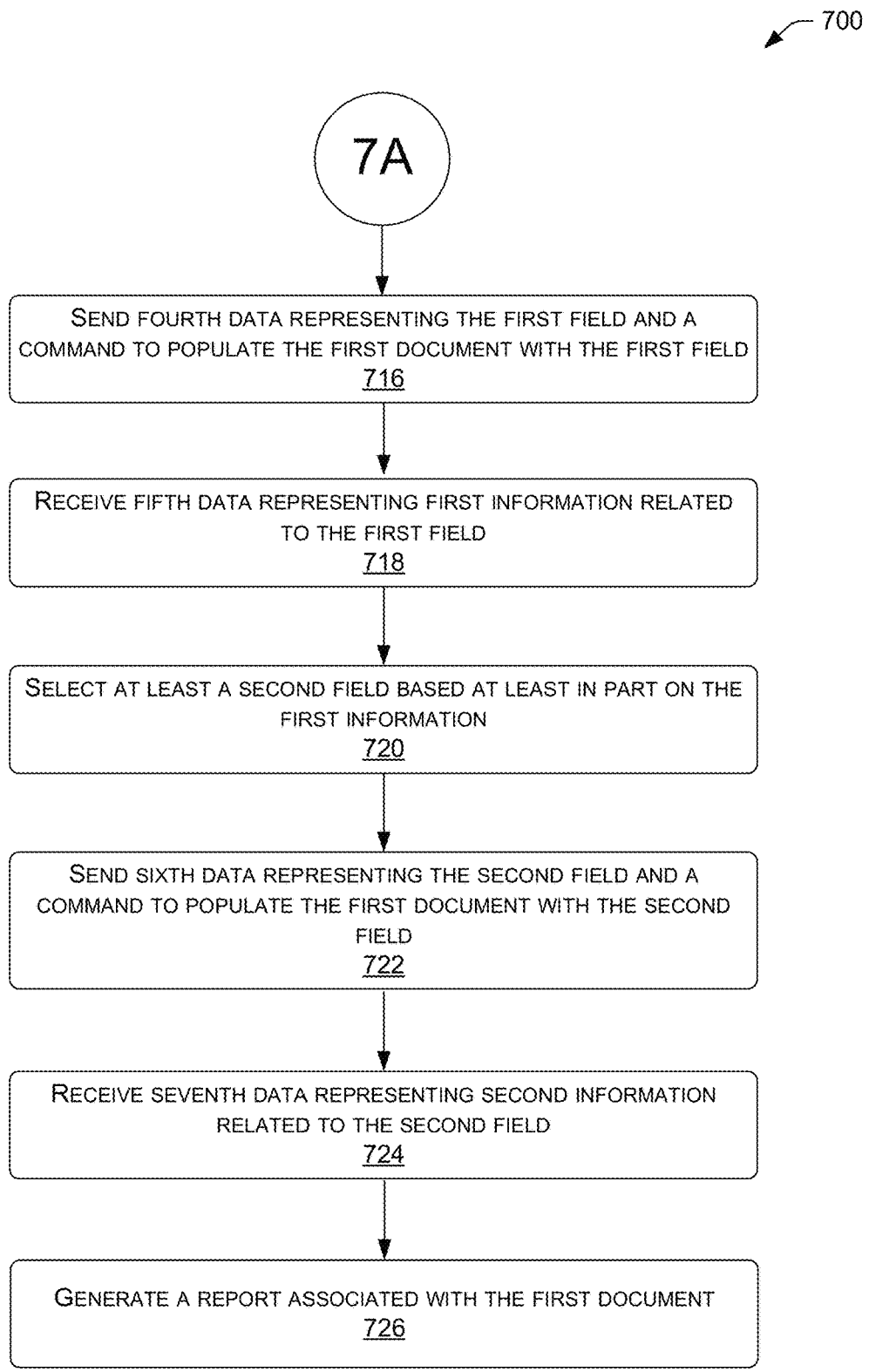

FIGS. 7A-7B illustrate a flow diagram of an example process 700 for updating fields of a document as information is being input into the document, according to various examples of the present disclosure. Even though the example process 700 of FIGS. 7A-7B is described as being performed by the remote system 102, in other examples, at least some of the example process 700 of FIGS. 7A-7B can be performed by one or more other electronic devices. For example, at least some of the example process 700 of FIGS. 7A-7B can be performed by the electronic device 104 and/or the electronic device 202.

At block 702, the process 700 includes storing first data representing a first document associated with a first type of user. For example, the remote system 102 can store the first data representing the first document associated with the first type of user. In some examples, the first data can further represent an identifier associated with the first type of user. In some examples, types of user can include, but are not limited to, doctors, nurses, managers, associates, employees, and/or any other type of position within a group, business, corporation, medical facility, and/or so forth.

At block 704, the process 700 includes storing second data representing a second document associated with a second type of user. For example, the remote system 102 can store the second data representing the second document associated with the second type of user. In some examples, the second data can further represent an identifier associated with the second type of user.

At 706, the process 700 includes receiving third data representing the first type of user. For example, the remote system 102 can receive, from an electronic device, the third data representing the first type of user. In some examples, the third data can represent an identifier associated with the first type of user. In some examples, the third data can further represent a request for the first document.

At 708, the process 700 includes selecting the first document based at least in part on the third data. For example, the remote system 102 can select the first document based at least in part on the third data representing the first type of user. In some examples, to select the first document, the remote system 102 can match the identifier represented by the third data to the identifier represented by the first data. Based at least in part on the match, the remote system 102 can select the first document.

At 710, the process 700 includes sending the first data representing the first document. For example, the remote system 102 can send, to the electronic device, the first data representing the first document. In some examples, the sending of the first data can cause the electronic device to display the first document. In some examples, the first document can include one or more initial fields. For example, if the first document is associated with obtaining information associated with a patient, the one or more initial fields can include a field for inputting an initial diagnosis associated with the patient.

At 712, the process 700 includes determining a type of diagnosis. For example, the remote system 102 can determine the type of diagnosis. In some examples, the remote system 102 can determine the type of diagnosis based at least in part on receiving, from the electronic device, data representing the type of diagnosis. In some examples, the remote system 102 can determine the type of diagnosis by analyzing one or more reports previously generated for the patient. For example, the one or more reports can indicate that the patient has the type of diagnosis.

At 714, the process 700 includes selecting at least a first field based at least in part on the type of diagnosis. For example, the remote system 102 can select the at least the first field based at least in part on the type of diagnosis. In some examples, the at least the first field can correspond to one or more questions associated with the type of diagnosis. For example, the one or more questions can be asking for information related to one or more symptoms associated with the type of diagnosis.

At 716, the process 700 includes sending fourth data representing the first field and a command to populate the first document with the first field. For example, the remote system 102 can send, to the electronic device, the fourth data representing the first field and the command to populate the first document with the first field. In some examples, the fourth data can cause the electronic device to display the first field as part of the first document.

At 718, the process 700 includes receiving fifth data representing first information related to the first field. For example, the remote system 102 can receive, from the electronic device, the fifth data representing the first information related to the first field. In some examples, based at least in part on receiving the fifth data, the remote system 102 can determine a first correlation score associated with the first information. The remote system 102 can then determine whether the first correlation score satisfies a threshold score.

At 720, the process 700 includes selecting at least a second field based at least in part on the first information. For example, the remote system 102 can select the at least the second field based at least in part on the first information. In some examples, the at least the second field can correspond to one or more questions associated with the type of diagnosis. For example, the one or more questions can be asking for further information related to the one or more symptoms associated with the type of diagnosis. In some examples, the at least the second field can further correspond to one or more questions associated with the first information. For example, the one or more questions can be asking for further information that clarifies the first information.

At 722, the process 700 includes sending sixth data representing the second field and a command to populate the first document with the second field. For example, the remote system 102 can send, to the electronic device, the sixth data representing the second field and the command to populate the first document with the second field. In some examples, the sixth data can cause the electronic device to display the second field as part of the first document.

At 724, the process 700 includes receiving seventh data representing second information related to the second field. For example, the remote system 102 can receive, from the electronic device, the seventh data representing the second information related to the second first field. In some examples, based at least in part on receiving the seventh data, the remote system 102 can determine a second correlation score associated with the first information and/or the second information. The remote system 102 can then determine whether the second correlation score satisfies the threshold score.

At 726, the process 700 includes generating a report associated with the first document. For example, the remote system 102 can generate the report associated with the first document. In some examples, the report can indicate at least the first field, the first information, the second field, and the second information. The remote system 102 can then store data representing the report in one or more databases.

Figure 8:
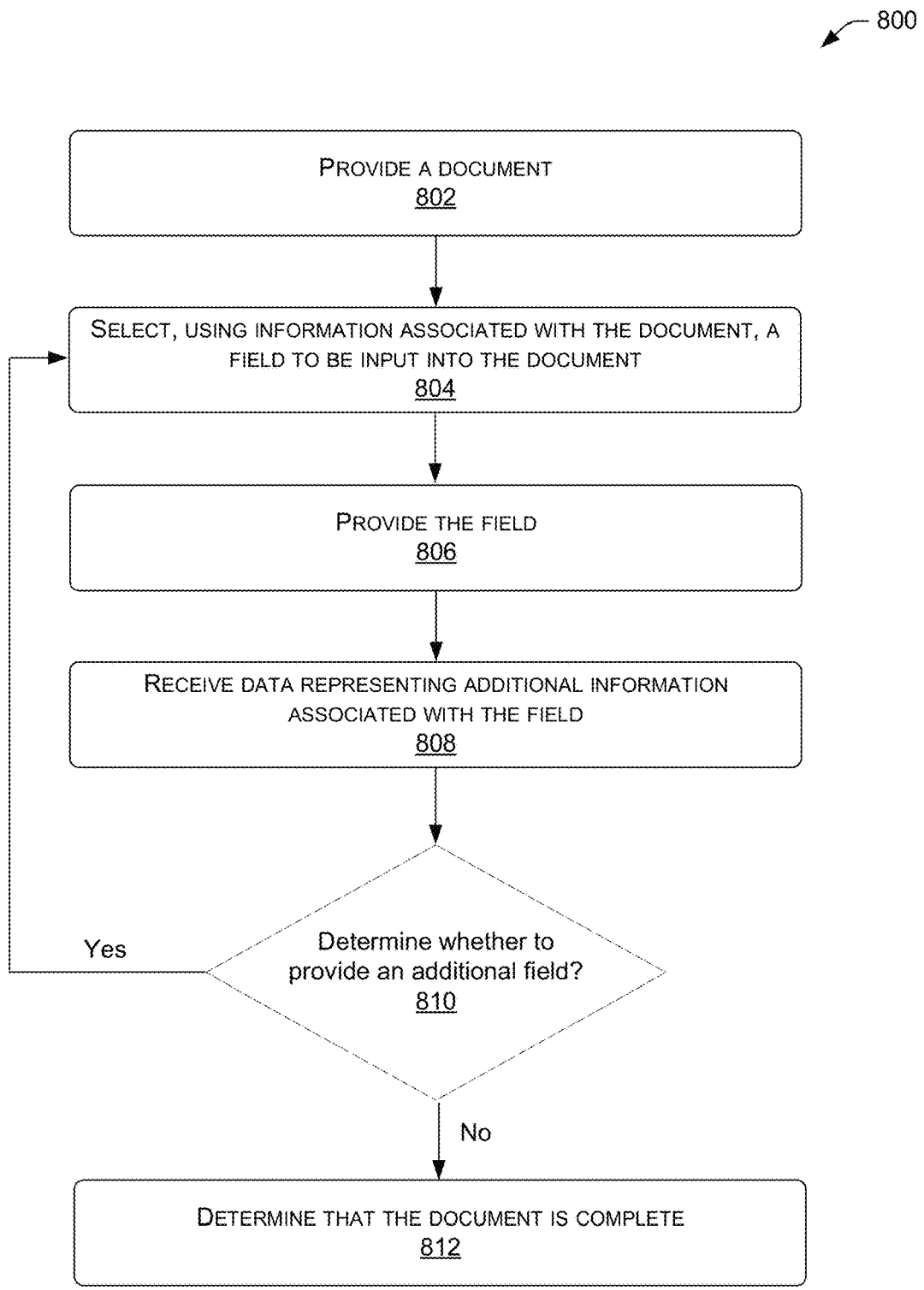
FIG. 8 illustrates a flow diagram of an example process for updating fields of a document, according to various examples of the present disclosure.

FIG. 8 illustrates a flow diagram of an example process 800 for updating fields of a document, according to various examples of the present disclosure. Even though the example process 800 of FIG. 8 is described as being performed by the remote system 102, in other examples, at least some of the example process 800 of FIG. 8 can be performed by one or more other electronic devices. For example, at least some of the example process 800 of FIG. 8 can be performed by the electronic device 104 and/or the electronic device 202.

At 802, the process 800 includes providing a document. For example, the remote system 102 can send, to an electronic device, data representing the document. In some examples, the remote system 102 provides the document based at least in part on receiving, from the electronic device, data representing a request for the document. In some examples, the document is associated with a type of user that is using the electronic device.

At 804, the process 800 includes selecting, using information associated with the document, a field to be input into the document. For example, the remote system 102 can select the field using information that is included within the document. In some examples, the information can indicate a diagnosis of a patient. In some examples, the information can be related to one or more other fields included within the document.

At 806, the process 800 includes providing the field. For example, the remote system 102 can send, to the electronic device, data representing the field. In some examples, the data can further include a command to input the field into the document. In some examples, the data causes the electronic device to input the field into the document.

At 808, the process 800 includes receiving data representing additional information associated with the field. For example, the remote system 102 can receive, from the electronic device, the data representing the additional information associated with the field. In some examples, the remote system 102 can then store the data within one or more databases.

At 810, the process 800 includes determining whether to provide an additional field. For example, the remote system 102 can determine whether to provide an additional field for the document. In some examples, to make the determination, the remote system 102 can analyze the information and, based at least in part on the analysis, determine a correlation score. The remote system 102 can then determine not to provide the additional field when the correlation score satisfies a threshold score, but determine to provide the additional field when the correlation score does not satisfy the threshold score. In some examples, to make the determination, the remote system 102 can determine whether a period of time has elapsed. The remote system 102 can then determine not to provide the additional field when the period of time has elapsed, but determine to provide the additional field when the period of time has not yet elapsed. Still, in some examples, the remote system 102 can determine not to provide the additional field based at least in part on receiving, from the electronic device, data indicating that the document is complete.

If at 810 it is determined to provide the additional field, then the process 800 can repeat back at 804. However, if at 810 it is determined to not provide the additional field, then at 812, the process 800 includes determining that the document is complete. For example, the remote system 102 can determine that the document is complete. In some examples, the remote system 102 can then generate a report associated with the document.

Figure 9:
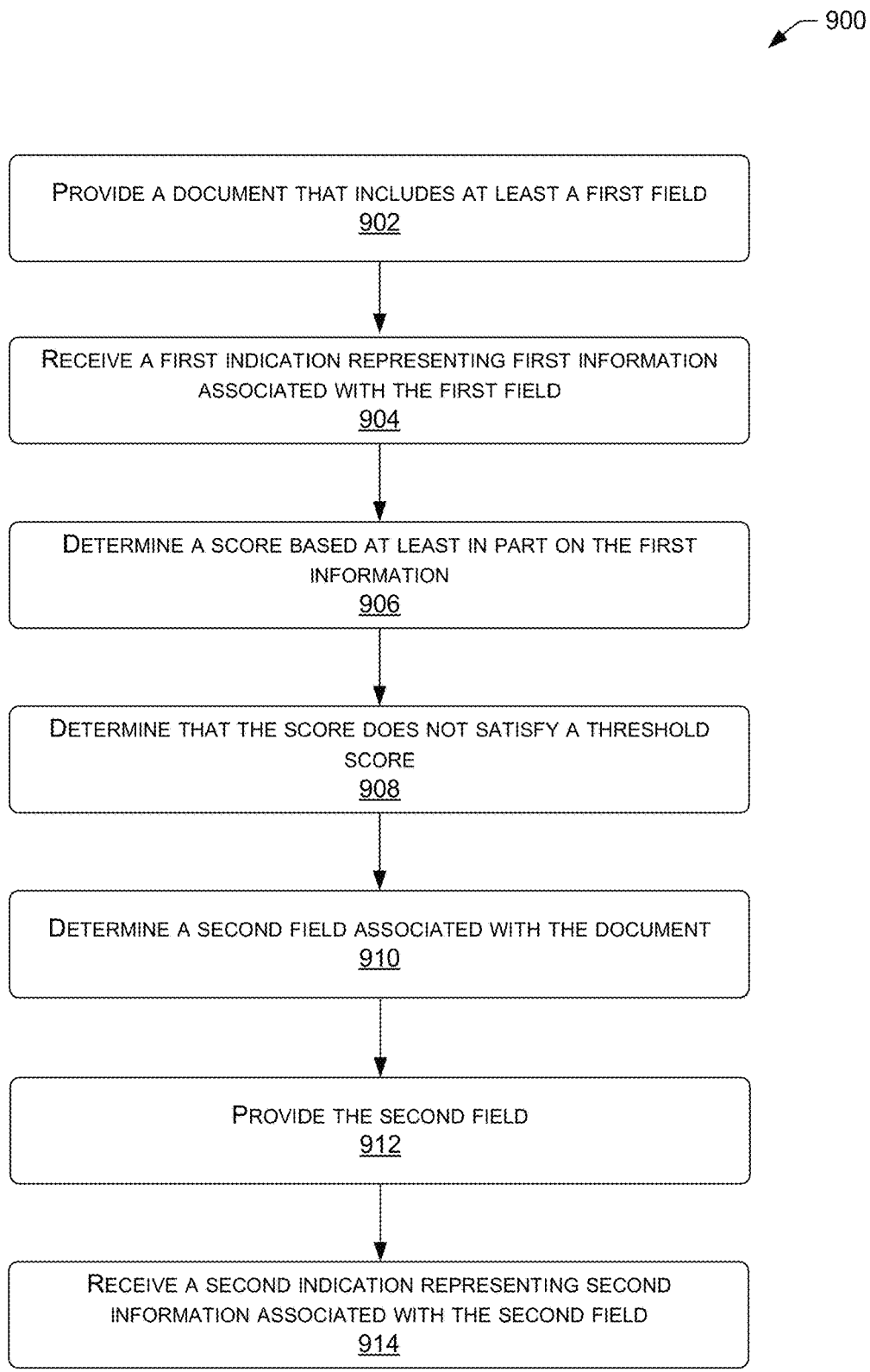
FIG. 9 illustrates a flow diagram of an example process for using scores to determine whether a document is complete, according to various examples of the present disclosure.

FIG. 9 illustrates a flow diagram of an example process 800 for using scores to determine whether a document is complete, according to various examples of the present disclosure. Even though the example process 900 of FIG. 9 is described as being performed by the remote system 102, in other examples, at least some of the example process 900 of FIG. 9 can be performed by one or more other electronic devices. For example, at least some of the example process 900 of FIG. 9 can be performed by the electronic device 104 and/or the electronic device 202.

At 902, the process 900 includes providing a document that includes at least a first field. For example, the remote system 102 can send, to an electronic device, data representing the document that includes the first field. In some examples, the remote system 102 provides the document based at least in part on receiving, from the electronic device, data representing a request for the document. In some examples, the document is associated with a type of user that is using the electronic device.

At 904, the process 900 includes receiving a first indication representing first information associated with the first field. For example, the remote system 102 can receive, from the electronic device, data indicating the first information associated with the first field. In some examples, if the first field includes a first question, the first information can correspond to a response to the first question.

At 906, the process 900 includes determining a score based at least in part on the first information. For example, the remote system 102 can determine the score based at least in part on the first information. In some examples, if the document is associated with diagnosing a patient, the score can indicate a likelihood that an initial diagnosis for the patient is correct (e.g., the patient has the disease). In such examples, the score can be greater when the first information indicates that the patient is experience one or more symptoms associated with the disease, but be lower when the first information indicates that the patient is not experiencing one or more symptoms associated with the disease.

At 908, the process 900 includes determining that the score does not satisfy a threshold score. For example, the remote system 102 can determine that the score does not satisfy the threshold score. In some examples, based at least in part on the determination, the remote system 102 can determine to provide additional fields for the document.

At 910, the process 900 includes determining a second field associated with the document. For example, the remote system 102 can determine the second field associated with the document. In some examples, the remote system 102 determines the second field using the first information. For example, the second field can correspond to a second question related to the first information. For instance, the second question can inquire about more details to the first information.

At 912, the process 900 includes providing the second field. For example, the remote system 102 can send, to the electronic device, data representing the second field. In some examples, the data can further represent a command to populate the document with the second field.

At 914, the process 900 includes receiving a second indication representing second information associated with the second field. For example, the remote system 102 can receive, from the electronic device, data indicating the second information associated with the second field. In some examples, if the second field includes the second question, the second information can correspond to a response to the second question. In some examples, the remote system 102 can then determine an additional score using the first information and/or the second information. In such examples, if the additional score satisfies the threshold score, then the remote system 102 can determine that the document is complete. However, if the additional score does not satisfy the threshold score, then the remote system 102 can continue to provide additional fields to be added to the document.

Figure 10:
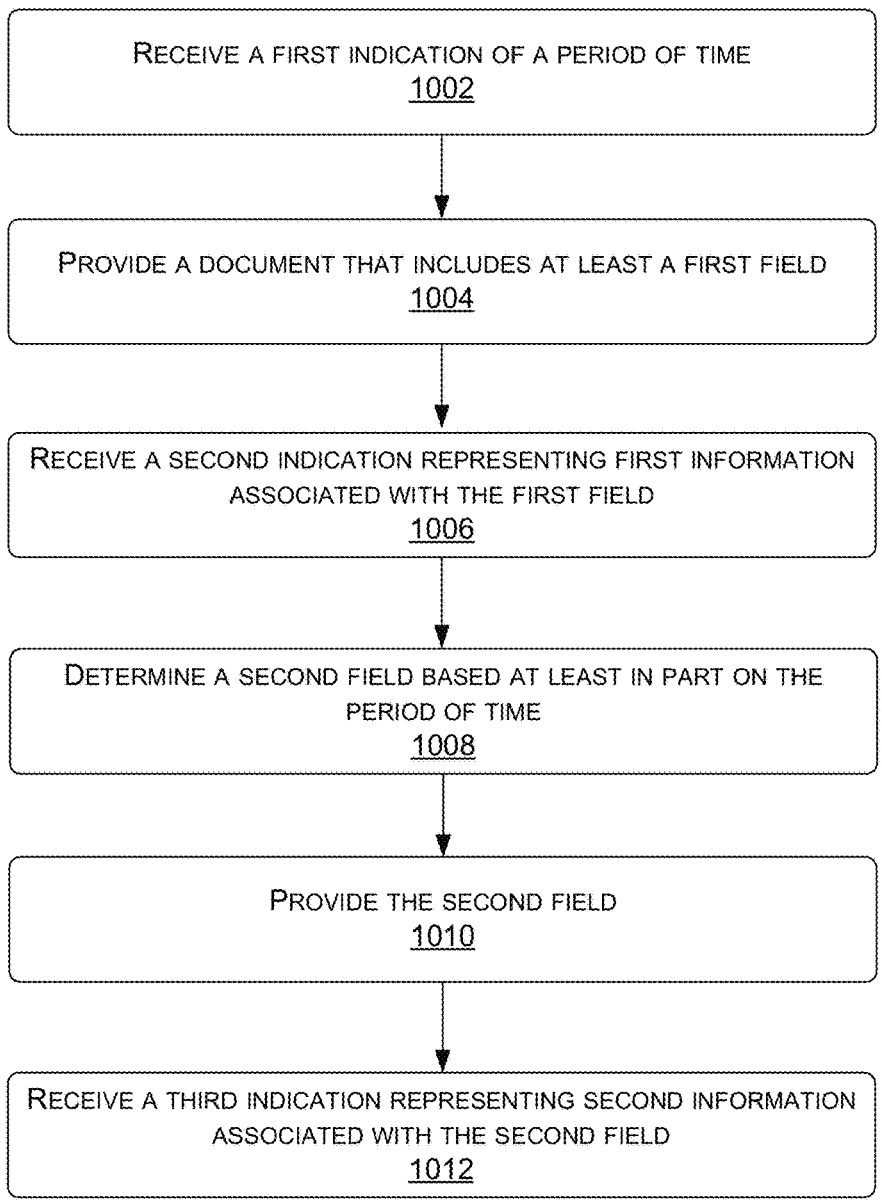
FIG. 10 illustrates a flow diagram of an example process for using a period of time to select at least one field for a document, according to various examples of the present disclosure.

FIG. 10 illustrates a flow diagram of an example process 1000 for using a period of time to select at least one field for a document, according to various examples of the present disclosure. Even though the example process 1000 of FIG. 10 is described as being performed by the remote system 102, in other examples, at least some of the example process 1000 of FIG. 10 can be performed by one or more other electronic devices. For example, at least some of the example process 1000 of FIG. 10 can be performed by the electronic device 104 and/or the electronic device 202.

At 1002, the process 1000 includes receiving a first indication of a period of time. For example, the remote system 102 can receive the first indication of the period of time. In some examples, to receive the first indication, the remote system 102 can receive, from an electronic device, data representing the period of time. In some examples, to receive the first indication, the remote system 102 can receive data indicating a document type associated with the document. The remote system 102 can then determine the period of time based at least in part on the document type.

At 1004, the process 1000 includes providing a document that includes at least a first field. For example, the remote system 102 can send, to the electronic device, data representing the document that includes the first field. In some examples, the remote system 102 provides the document based at least in part on receiving, from the electronic device, data representing a request for the document. In some examples, the document is associated with a type of user that is using the electronic device.

At 1006, the process 1000 includes receiving a second indication representing first information associated with the first field. For example, the remote system 102 can receive, from the electronic device, data indicating the first information associated with the first field. In some examples, if the first field includes a first question, the first information can correspond to a response to the first question.

At 1008, the process 1000 includes determining a second field based at least in part on the period of time. For example, the remote system 102 can determine the second field based at least in part on the period of time. In some examples, the remote system 102 can further determine the second field based at least in part on the first information.

At 1010, the process 1000 includes providing the second field. For example, the remote system 102 can send, to the electronic device, data representing the second field. In some examples, the data can further represent a command to populate the document with the second field.

At 1014, the process 1000 includes receiving a third indication representing second information associated with the second field. For example, the remote system 102 can receive, from the electronic device, data indicating the second information associated with the second field. In some examples, if the second field includes the second question, the second information can correspond to a response to the second question.

Figure 11:
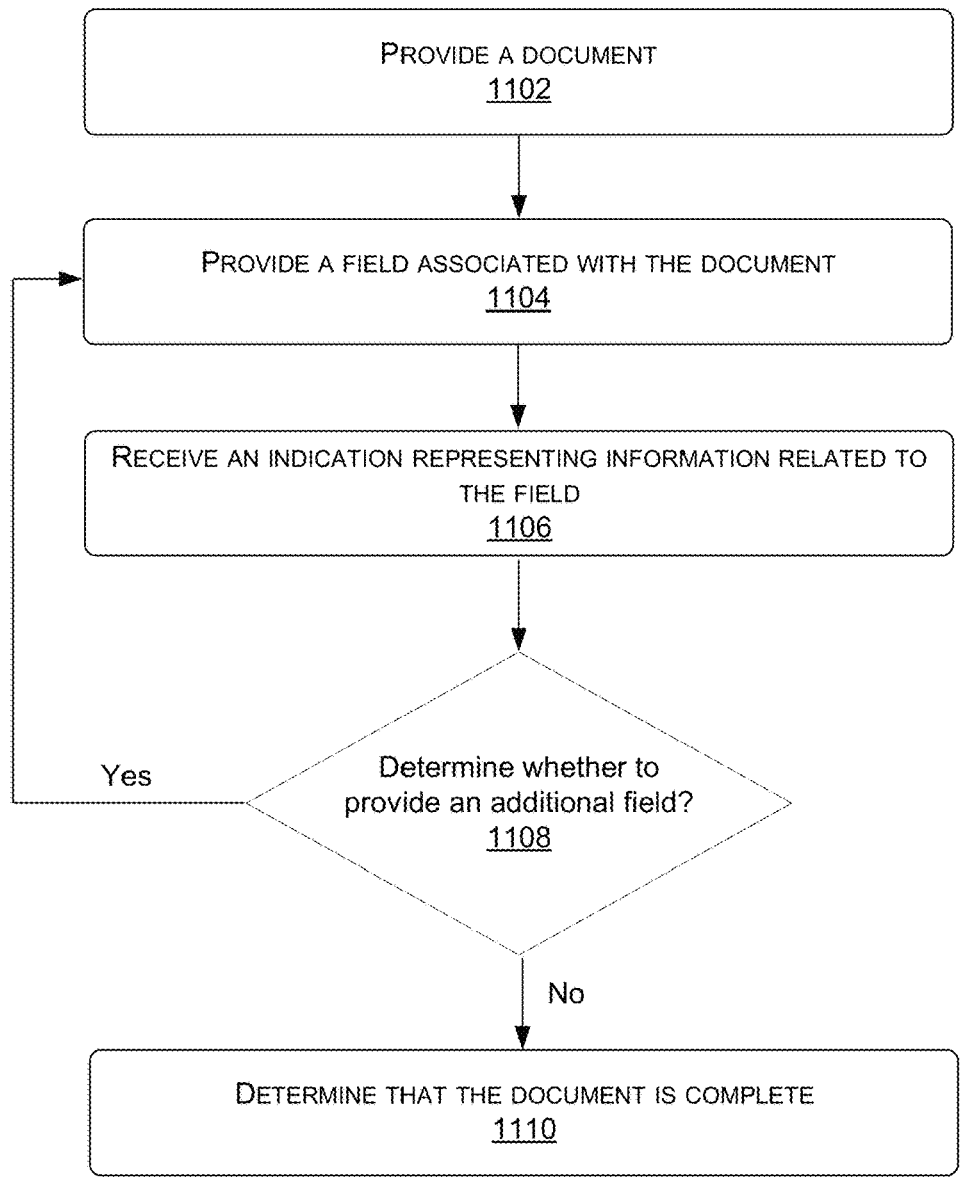
FIG. 11 illustrates a flow diagram of an example process for an electronic device updating fields of a document, according to various examples of the present disclosure.

FIG. 11 illustrates a flow diagram of an example process 1100 for an electronic device updating fields of a document, according to various examples of the present disclosure. At 1102, the process 1100 includes providing a document. For example, the electronic device can display the document. In some examples, before displaying the document, the electronic device can receive, from the remote system 102, data representing the document. In some examples, the electronic device provides the document based at least in part on receiving an input associated with providing the document.

At 1104, the process 1100 includes providing a field associated with the document. For example, the electronic device can display the field associated with the document. In some examples, the electronic device displays the field after selecting the field for the document. In some examples, the electronic device displays the field after receiving, from the remote system 102, data representing the field.

At 1106, the process 1100 includes receiving an indication representing information related to the field. For example, the electronic device can receive an input indicating the information related to the field. In some examples, based at least in part on the input, the electronic device can add the information to the document. In some examples, based at least in part on the input, the electronic device can send, to the remote system 102, data representing the information.

At 1108, the process 1100 includes determining whether to provide an additional field. For example, the electronic device can determine whether to provide an additional field for the document. In some examples, to make the determination, the electronic device can analyze the information and, based at least in part on the analysis, determine a correlation score. The electronic device can then determine not to provide the additional field when the correlation score satisfies a threshold score, but determine to provide the additional field when the correlation score does not satisfy the threshold score. In some examples, to make the determination, the electronic device can determine whether a period of time has elapsed. The electronic device can then determine not to provide the additional field when the period of time has elapsed, but determine to provide the additional field when the period of time has not yet elapsed.

In some examples, to make the determination, the electronic device can determine whether an input was received indicating that the document is complete. The electronic device can then determine not to provide the additional field when the input is received, but determine to provide the additional field when the input has yet to be received. Still, in some examples, to make the determination, the electronic device can determine whether the electronic device has received, from the remote system 102, data representing the additional field. The electronic device can then determine not to provide the additional field when the data has not been received, but determine to provide the additional field when the data has been received.

If at 1108 it is determined to provide the additional field, then the process 1100 can repeat back at 1104. However, if at 1108 it is determined to not provide the additional field, then at 1110, the process 1100 includes determining that the document is complete. For example, if the electronic device determines not to provide the additional field, then the electronic device can determine that the document is complete.

While the foregoing invention is described with respect to the specific examples, it is to be understood that the scope of the invention is not limited to these specific examples. Since other modifications and changes varied to fit particular operating requirements and environments will be apparent to those skilled in the art, the invention is not considered limited to the example chosen for purposes of disclosure, and covers all changes and modifications which do not constitute departures from the true spirit and scope of this invention.

Although the application describes embodiments having specific structural features and/or methodological acts, it is to be understood that the claims are not necessarily limited to the specific features or acts described. Rather, the specific features and acts are merely illustrative some embodiments that fall within the scope of the claims of the application.

What is claimed is:

1. A computing device comprising:
one or more processors; and
one or more non-transitory computer-readable media storing instructions that, when executed, cause the computing device to perform operations comprising:
sending, to an electronic device, a document that includes at least a first field, the first field associated with requesting first information related to determining a type of diagnosis associated with a patient;
receiving, from the electronic device, the first information;
determining, based at least in part on the first information, a score representing a probability that the first information is indicative of the type of diagnosis associated with the patient;
determining that the score does not satisfy a threshold score;
based at least in part on the score not satisfying the threshold score, determining a second field that is associated with requesting second information related to determining the type of diagnosis associated with the patient;
causing the electronic device to populate the document with the second field; and
receiving, from the electronic device, the second information associated with the second field.

2. The computing device of claim 1, the operations further comprising:
determining an updated score based at least in part on the second information;
determining that the updated score satisfies the threshold score; and
based at least in part on the updated score satisfying the threshold score, refraining from determining a third field that is associated with requesting third information related to determining the type of diagnosis or another type of diagnosis associated with the patient.

3. The computing device of claim 1, the operations further comprising storing a first rule associating the first information with the second field, wherein determining the second field is further based at least in part on the first rule.

4. The computing device of claim 1, the operations further comprising:
determining an updated score based at least in part on the second information;
determining that the updated score satisfies the threshold score; and determining the type of diagnosis based at least in part on the updated score satisfying the threshold score.

5. The computing device of claim 1, wherein the document is a first document of multiple documents, the operations further comprising:
receiving an indication of a type of user of the electronic device; and
selecting the first document from the multiple documents based at least in part on the type of user, wherein the first document is related to the type of user and is distinguishable from another document of the multiple documents, the other document related to another type of user.

6. The computing device of claim 1, wherein the type of diagnosis is a first type of diagnosis and the document further includes a third field associated with requesting third information related to determining a second type of diagnosis associated with the patient, the second type of diagnosis being distinguishable from the first type of diagnosis.

7. The computing device of claim 1, wherein sending the document to the electronic device comprises sending the document to the electronic device at a first instance of time, the operations further comprising:
receiving, at a second instance of time and from the electronic device, a request to provide the document;
based at least in part on a length of a period of time between the first instance of time and the second instance of time, altering the document such that at least the first field of the document comprises a different context that is associated with requesting third information related to determining the type of diagnosis; and
sending the document to the electronic device at a third instance of time to request the third information.

8. The computing device of claim 1, the operations further comprising generating a report that includes at least:
the first field;
the first information;
the second field; and
the second information.

9. One or more non-transitory computer-readable media storing instructions that, when executed, cause one or more computing devices to perform operations comprising:
sending, to an electronic device, a document that includes at least a first field, the first field associated with requesting first information related to determining a type of diagnosis associated with a patient;
receiving, from the electronic device, the first information;
determining, based at least in part on the first information, a score representing a probability that the first information is indicative of the type of diagnosis associated with the patient;
determining that the score does not satisfy a threshold score;
based at least in part on the score not satisfying the threshold score, determining a second field that is associated with requesting second information related to determining the type of diagnosis associated with the patient;
causing the electronic device to populate the document with the second field; and
receiving, from the electronic device, the second information associated with the second field.

10. The one or more non-transitory computer-readable media of claim 9, the operations further comprising storing a first rule associating the first information with the second field, wherein determining the second field is further based at least in part on the first rule.

11. The one or more non-transitory computer-readable media of claim 9, the operations further comprising:
determining an updated score based at least in part on the second information;
determining that the updated score satisfies the threshold score; and
based at least in part on the updated score satisfying the threshold score, refraining from determining a third field that is associated with requesting third information related to determining the type of diagnosis or another type of diagnosis associated with the patient.

12. The one or more non-transitory computer-readable media of claim 9, the operations further comprising:
determining an updated score based at least in part on the second information;
determining that the updated score satisfies the threshold score; and
determining the type of diagnosis based at least in part on the updated score satisfying the threshold score.

13. The one or more non-transitory computer-readable media of claim 9, wherein the document is a first document of multiple documents, the operations further comprising:
receiving an indication of a type of user of the electronic device; and
selecting the first document from the multiple documents based at least in part on the type of user, wherein the first document is related to the type of user and is distinguishable from another document of the multiple documents, the other document related to another type of user.

14. The one or more non-transitory computer-readable media of claim 9, wherein the type of diagnosis is a first type of diagnosis and the document further includes a third field associated with requesting third information related to determining a second type of diagnosis associated with the patient, the second type of diagnosis being distinguishable from the first type of diagnosis.

15. The one or more non-transitory computer-readable media of claim 9, wherein sending the document to the electronic device comprises sending the document to the electronic device at a first instance of time, the operations further comprising:
receiving, at a second instance of time and from the electronic device, a request to provide the document;
based at least in part on a length of a period of time between the first instance of time and the second instance of time, altering the document such that at least the first field of the document comprises a different context that is associated with requesting third information related to determining the type of diagnosis; and
sending the document to the electronic device at a third instance of time to request the third information.

16. The one or more non-transitory computer-readable media of claim 9, the operations further comprising generating a report that includes at least:
the first field;
the first information;
the second field; and
the second information.

17. A system comprising:
one or more processors; and
one or more non-transitory computer-readable media storing instructions that, when executed, cause the one or more processors to perform operations comprising:

providing, at a first time, a document to an electronic device, the document including at least a first field comprising a first question, the first question associated with requesting first information related to a type of diagnosis associated with a user;

receiving the first information from the electronic device;

providing, at a second time, the document to the electronic device;

determining a period of time between the first time and the second time;

based at least in part on the period of time meeting or exceeding a threshold period of time, altering the document such that the first field of the document comprises a second question instead of the first question, the second question associated with requesting second information related to the type of diagnosis; and sending, to the electronic device, the document including at least the first field comprising the second question.

18. The system of claim 17, the operations further comprising:

receiving, from the electronic device, a response to the second question, the response including the second information; and determining a score based at least in part on the second information, the score representing a probability that the second information is indicative of the type of diagnosis.

19. The system of claim 18, the operations further comprising:

determining that the score satisfies a threshold score; and determining the type of diagnosis based at least in part on the updated score satisfying the threshold score.

20. The system of claim 18, the operations further comprising:

determining that the score does not satisfy a threshold score; and determining another type of diagnosis associated with the patient based at least in part on the score not satisfying the threshold score.

* * * * *